United States Patent
Lee et al.

(10) Patent No.: US 10,193,088 B2
(45) Date of Patent: Jan. 29, 2019

(54) PEROVSKITE NANOCRYSTALLINE PARTICLES AND OPTOELECTRONIC DEVICE USING SAME

(71) Applicant: POSTECH ACADEMY-INDUSTRY FOUNDATION, Pohang-si, Gyeongsangbuk-do (KR)

(72) Inventors: Tae-Woo Lee, Pohang-si (KR); Sanghyuk Im, Hwaseong-si (KR); Young-Hoon Kim, Daegeon (KR); Himchan Cho, Daegu (KR)

(73) Assignee: POSTECH ACADEMY-INDUSTRY FOUNDATION, Pohang-si (KR)

(*) Notice: Subject to any disclaimer, the term of this patent is extended or adjusted under 35 U.S.C. 154(b) by 0 days.

(21) Appl. No.: 15/524,421

(22) PCT Filed: Nov. 6, 2015

(86) PCT No.: PCT/KR2015/011959
§ 371 (c)(1),
(2) Date: Jul. 26, 2017

(87) PCT Pub. No.: WO2016/072805
PCT Pub. Date: May 12, 2016

(65) Prior Publication Data
US 2017/0358757 A1    Dec. 14, 2017

(30) Foreign Application Priority Data

| Nov. 6, 2014 | (KR) | 10-2014-0153968 |
| Nov. 6, 2014 | (KR) | 10-2014-0153975 |
| Nov. 6, 2015 | (KR) | 10-2015-0156172 |

(51) Int. Cl.
*H01L 51/00* (2006.01)
*C01G 21/16* (2006.01)
(Continued)

(52) U.S. Cl.
CPC .......... *H01L 51/0077* (2013.01); *C01G 21/16* (2013.01); *C07F 7/24* (2013.01);
(Continued)

(58) Field of Classification Search
CPC ............. H01L 51/0077; H01L 51/0037; H01L 51/004; H01L 51/0072; H01L 51/442;
(Continued)

(56) References Cited

U.S. PATENT DOCUMENTS

| 8,109,153 | B2 * | 2/2012 | Kirst | ...................... G01F 1/849 |
| | | | | 73/861.357 |
| 2005/0061363 | A1 * | 3/2005 | Ginley | ................... B82Y 30/00 |
| | | | | 136/252 |
| 2010/0129529 | A1 * | 5/2010 | Shin | ....................... B82Y 30/00 |
| | | | | 427/66 |

FOREIGN PATENT DOCUMENTS

| KR | 10-2001-0015084 | 2/2001 |
| KR | 10-2014-0007045 | 1/2014 |

(Continued)

OTHER PUBLICATIONS

Smith et al., "Semiconductor Nanocrystals: Structure, Properties, and Band Gap Engineering", 2010, Acc Chem Res Feb. 16, 2010, 43(2).*

(Continued)

*Primary Examiner* — Nikolay Yushin
(74) *Attorney, Agent, or Firm* — Lex IP Meister, PLLC

(57) ABSTRACT

Provided are perovskite nanocrystalline particle and an optoelectronic device using the same. The perovskite nanocrystalline particle may include a perovskite nanocrystalline structure while being dispersible in an organic solvent. Accordingly, the perovskite nanocrystalline particle in accordance with the present invention has therein a perovskite nanocrystal having a crystalline structure in which FCC and BCC are combined; can form a lamellar structure (Continued)

in which an organic (or A site) plane and an inorganic plane are alternately stacked; and can show high color purity since excitons are confined to the inorganic plane.

20 Claims, 22 Drawing Sheets

(51) Int. Cl.
| | |
|---|---|
| *C09K 11/66* | (2006.01) |
| *C07F 7/24* | (2006.01) |
| *C09K 11/06* | (2006.01) |
| *C09K 11/02* | (2006.01) |
| *B82Y 20/00* | (2011.01) |
| *B82Y 30/00* | (2011.01) |
| *B82Y 40/00* | (2011.01) |
| *H01L 51/42* | (2006.01) |
| *H01L 51/44* | (2006.01) |
| *H01L 51/50* | (2006.01) |
| *H01L 51/52* | (2006.01) |
| *H01L 51/56* | (2006.01) |

(52) U.S. Cl.
CPC .......... *C09K 11/02* (2013.01); *C09K 11/025* (2013.01); *C09K 11/06* (2013.01); *C09K 11/665* (2013.01); *H01L 51/004* (2013.01); *H01L 51/0037* (2013.01); *H01L 51/0072* (2013.01); *B82Y 20/00* (2013.01); *B82Y 30/00* (2013.01); *B82Y 40/00* (2013.01); *C01P 2002/34* (2013.01); *C01P 2002/60* (2013.01); *C01P 2004/64* (2013.01); *C01P 2004/80* (2013.01); *C01P 2006/40* (2013.01); *C09K 2211/188* (2013.01); *H01L 51/424* (2013.01); *H01L 51/442* (2013.01); *H01L 51/5012* (2013.01); *H01L 51/5206* (2013.01); *H01L 51/5221* (2013.01); *H01L 51/56* (2013.01); *H01L 2251/301* (2013.01); *H01L 2251/308* (2013.01); *H01L 2251/558* (2013.01); *Y10S 977/774* (2013.01); *Y10S 977/788* (2013.01); *Y10S 977/814* (2013.01); *Y10S 977/892* (2013.01); *Y10S 977/896* (2013.01); *Y10S 977/948* (2013.01); *Y10S 977/95* (2013.01)

(58) Field of Classification Search
CPC ............... H01L 51/5012; H01L 51/424; H01L 51/5206; H01L 51/5221; H01L 51/56; H01L 2251/558; H01L 2251/308; H01L 2251/301; C09K 11/06; C09K 11/665; C09K 2211/188; C07F 7/24; C01G 21/16; C01P 2002/34; C01P 2002/60; C01P 2006/40; C01P 2004/80; C01P 2004/64; B82Y 40/00; B82Y 20/00; B82Y 30/00; Y10S 977/774; Y10S 977/788; Y10S 977/814; Y10S 977/896; Y10S 977/892; Y10S 977/95; Y10S 977/948
See application file for complete search history.

(56) References Cited

FOREIGN PATENT DOCUMENTS

| | | |
|---|---|---|
| KR | 10-2014-0035287 | 3/2014 |
| WO | 2013-171517 | 11/2013 |

OTHER PUBLICATIONS

Urban et al., "Synthesis of Single-Crystalline Perovskite Nanorods Composed of Barium Titanate and Strontium Titanate", 2002, J. Am. Chem. Soc., vol. 124, No. 7, pp. 1186-1187 (Jul. 2002).*

Viteri et al., "Quantum-chemical study of excitons in tetragonal BaTiO3 and SrTiO3 crystals", 2003, Proceedings of SPIE, vol. 5122, pp. 295-302, Feb. 2003.*

Koole et al., "Size Effect on Semiconductor Nanoparticles" 2014, Nanoparticles, Workhorses of Nanoscience, de Mello Donega, C (Ed.), Springer-Verlag Berlin Heidelberg 2014. pp. 13-51 (Oct. 2014).*

Suzuki et al., "Optical Band Gap of Barium Titanate Nanoparticles Prepared by RF-plasma Chemical Vapor Deposition", 2005, Jap Journal of Applied Physics, vol. 44, No. 4A pp. 2081-0282, published Apr. 8, 2005.*

Schmidt et al., "Nontemplate Synthesis of CH3NH3PbBr3 Perovskite Nanoparticles", 2014, J. Am. Chem. Soc., 2014, 136 (3), pp. 850-853, Publication Date : Jan. 3, 2014.*

O'Brien et al., "Synthesis of Monodisperse Nanoparticles of Barium Titanate: Toward a Generalized Strategy of Oxide Nanoparticle Synthesis", 2001, J. Am. Chem. Soc., vol. 123, pp. 12085-12086 (Dec. 2001).*

Junwu et al., "Solution-Phase Synthesis and Characterization of Perovskite LaCoO3 Nanocrystals via a Co-Precipitation Route", 2007, Journal of Rare Earths vol. 25 pp. 601-604 (Dec. 2007).*

Yu, Hui et al., "The Role of Chlorine in the Formation Process of 'CH3NH3PbI3-xClx' Perovskite", Advanced Functional Materials, Sep. 5, 2014, vol. 24, No. 45, pp. 7102-7108.

WIPO, International Search Report of PCT/KR2015/011959 dated Mar. 14, 2016.

Mali et al., Highly stable and efficient solid-state solar cells based on methylammonium lead bromide (CH3NH3PbBr3) perovskite quantum dots, pp. 1-9, Jun. 9, 2015, NPG Asia Materials.†

Schmidt et al., Nontemplate Synthesis of CH2NH3PbBr3 Perovskite Nanoparticles, pp. 850-853 and supplement S1-S17, Jan. 3, 2014, J. Am. Chem. Soc. 2014, 136, 850-853.†

\* cited by examiner
† cited by third party

FIG. 4
(a)
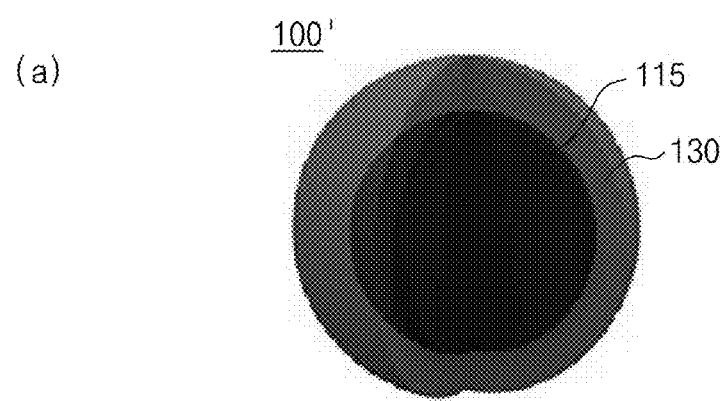
(b)
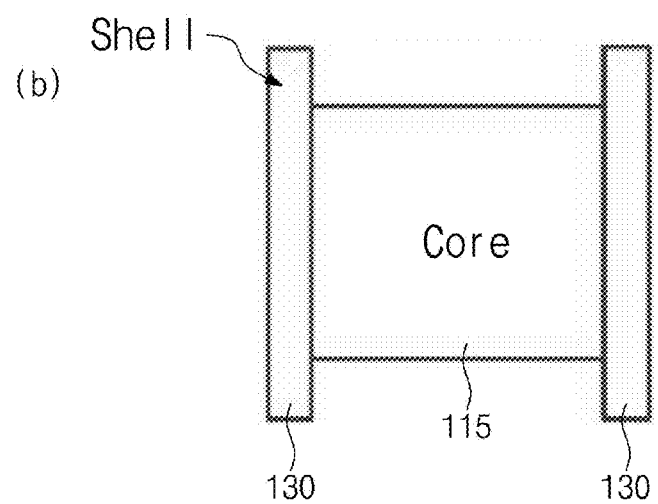

FIG. 7
(a)
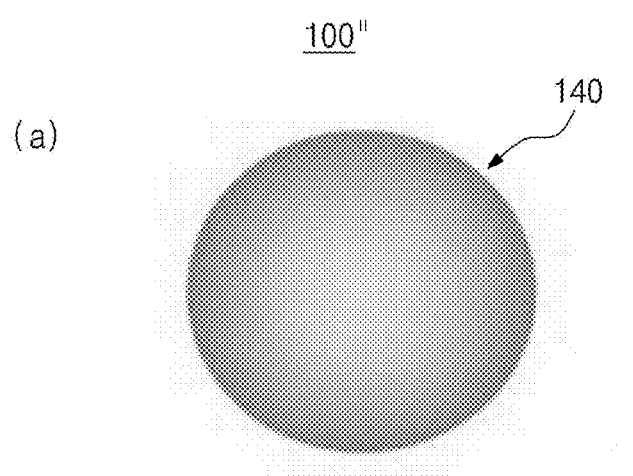
(b)
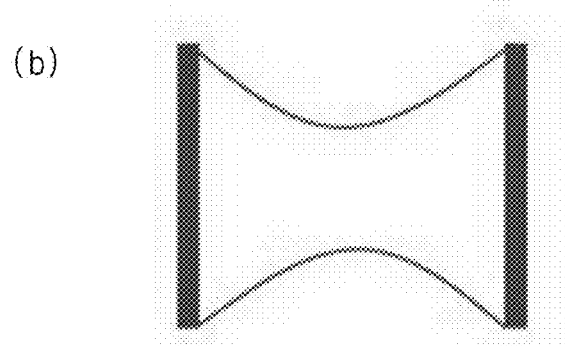

FIG. 10
(a)
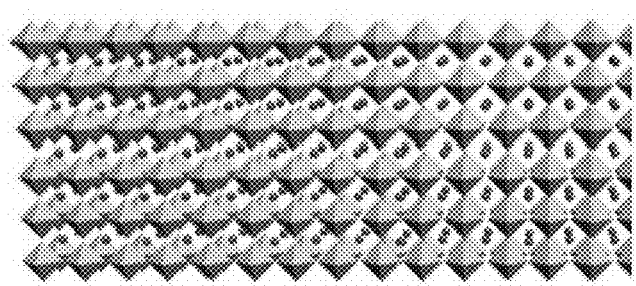
(b)
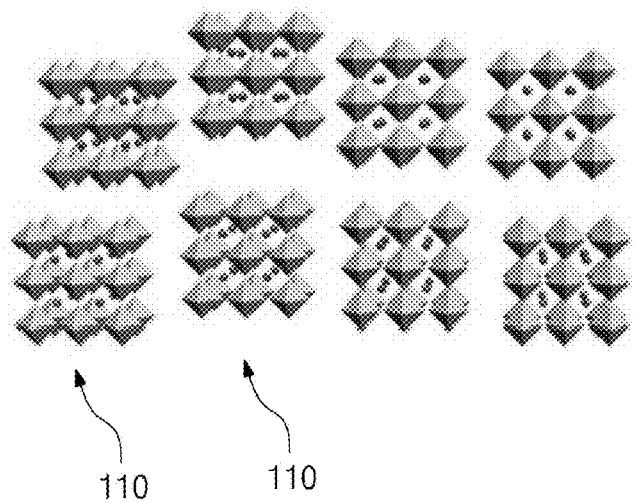
110  110

PEROVSKITE NANOCRYSTALLINE PARTICLES AND OPTOELECTRONIC DEVICE USING SAME

TECHNICAL FIELD

The present invention relates to a perovskite material, and more particularly, to an organic-inorganic-hybrid perovskite or inorganic metal halide perovskite nanocrystal particles and an optoelectronic device using the same.

BACKGROUND ART

The major trend of the display market is shifting from the existing high-efficiency and high-resolution-oriented display to the emotional image-quality display aiming at realizing a high color purity for demonstration of natural colors. From this viewpoint, while organic light emitting diode (OLED) devices using organic light-emitters have remarkably developed, inorganic quantum dot LEDs with the improved color purity have been actively researched and developed as alternatives. However, in terms of materials, both the organic light-emitters and the inorganic quantum dot light-emitters have intrinsic limitations.

The existing organic light-emitters have an advantage of high efficiency, but the existing organic light-emitters have a wide spectrum and poor color purity. Although the inorganic colloidal quantum dot light-emitters have been known to have high color purity because the luminescence occurs by quantum confinement effects or the quantum size effects, the luminescent color varies depending on the sizes of nanoparticles, each of which has a diameter of below 10 nm. There is a problem that it is difficult to uniformly control the sizes of the quantum dots as the color approaches the blue color, and thereby the size distribution deteriorates the color purity because of size distribution. Furthermore, because the inorganic quantum dots have a very deep valence band, there is a problem that it is difficult to inject holes because a hole injection barrier from an organic hole injection layer or an anode is too large. Also, both the light-emitters (organic emitters and inorganic quantum dot emitters) are disadvantageously expensive. Thus, there is a need for new types of hybrid organic-inorganic light-emitters that compensate for the disadvantages of the organic light-emitters and inorganic quantum dot emitters and maintains their merits.

Since the emitting materials based on hybrid of organic and inorganic materials (hereafter, organic-inorganic-hybrid) have advantages of low manufacturing costs and simple manufacturing and device manufacturing processes and also have all advantages of organic emitting materials, which are easy to control optical and electrical properties, and inorganic emitting materials having high charge mobility and mechanical and thermal stability, the organic-inorganic-hybrid emitting materials are attracting attention academically and industrially.

Among them, since the organic-inorganic-hybrid perovskite materials have high color purity, simple color control, and low synthesis costs, the organic-inorganic-hybrid perovskite materials are very likely to be developed as the light-emitters. The high color purity (full width at half maximum (FWHM)≈20 nm) from these materials can be realized because they have a layered structure in which a two-dimensional (2D) plane made of the inorganic material is sandwiched between 2D planes made of the organic material and a large difference in dielectric constant between the inorganic material and the organic material is large ($\varepsilon_{organic} \approx 2.4$, $\varepsilon_{inorganic} \approx 6.1$) so that the electron-hole pairs (or excitons) are bound to the inorganic 2D layer.

A material having the conventional perovskite structure ($ABX_3$) is inorganic metal oxide.

In general, the inorganic metal oxides are oxides, for example, materials in which metal (alkali metals, alkali earth metals, lanthanides, etc) cations such as Ti, Sr, Ca, Cs, Ba, Y, Gd, La, Fe, and Mn, which have sizes different from each other, are located in A and B sites, oxygen anions are located in an X site, and the metal cations in the B site are bonded to the oxygen anions in the X site in the corner-sharing octahedron form with the 6-fold coordination. Examples of the inorganic metal oxides include $SrFeO_3$, $LaMnO_3$, $CaFeO_3$, and the like.

On the other hand, since the organic-inorganic-hybrid perovskite has the $ABX_3$ in which organic ammonium ($RNH_3$) or inorganic cations are located in the A site, and halides (Cl, Br, I) are located in the X site to form the metal halide perovskite material, the organic-inorganic-hybrid perovskite are completely different from the inorganic metal oxide perovskite material in composition.

In addition, the materials vary in characteristics due to a difference in composition of the materials. The inorganic metal oxide perovskite typically has characteristics of superconductivity, ferroelectricity, colossal magnetoresistance, and the like, and thus has been generally conducted to be applied for sensors, fuel cells, memory devices, and the like. For example, yttrium barium copper oxides have superconducting or insulating properties according to oxygen contents.

On the other hand, since the organic-inorganic-hybrid perovskite (or inorganic metal halide perovskite) has a structure in which the organic plane (or "A site cation" plane in the perovskite crystal structure) and the inorganic plane are alternately stacked and thus has a structure similar to a lamellar structure so that the excitons are bound in the inorganic plane, it may be an ideal light-emitter that generally emits light having very high purity by the intrinsic crystal structure itself rather than the quantum size effect of the material.

If the organic-inorganic-hybrid perovskite has a chromophore (mainly including a conjugated structure) in which organic ammonium (or "A site cation" in perovskite crystals) has a bandgap less than that of an octahedron crystal structure composed of a central metal and a inorganic crystal structure ($BX_6$), the luminescence occurs in the organic ammonium. Thus, since light having high color purity is not emitted, a full width at half maximum of the luminescence spectrum becomes wider than 50 nm. Therefore, the organic-inorganic-hybrid perovskite are unsuitable for a light emitting layer. Thus, in this case, it is not very suitable for the light-emitter having the high color purity, which is highlighted in this patent. Therefore, in order to produce the light-emitter having the high color purity, it is important that the luminescence occurs in an inorganic lattice composed of the central metal-halogen elements without the organic ammonium which does not contain the chromophore. That is, this patent focuses on the development of the light-emitter having high color purity and high efficiency in the inorganic lattice.

For example, although an electroluminescent device in which an organic-inorganic-hybrid material containing an emitting dye is formed in the form of a thin film rather than that of a particle and used as a light emitting layer, the emission originated from the emitting-dye itself, not from the intrinsic perovskite lattice crystal structure, as is disclosed in Korean Patent Publication No. 10-2001-0015084 (Feb. 26, 2001).

However, since the organic-inorganic-hybrid perovskite or the inorganic metal halide perovskite has small exciton binding energy, there is a fundamental problem that the luminescence occurs at a low temperature, but the excitons do not efficiently emit light at room temperature due to thermal ionization and delocalization of a charge carrier and thus they are easily separated as free charge carriers and then annihilated. Also, there is a problem in that the excitons are annihilated by the layer having high conductivity in the vicinity of the excitons when the free charge carriers are recombined again to form excitons.

Therefore, there is a need to study the perovskite materials having the improved luminescence efficiencies that are capable of being applied to various electronic devices.

DISCLOSURE OF THE INVENTION

Technical Problem

To solve the abovementioned problems, the present invention provides nanocrystalline particles having improved luminescence efficiency and durability (or stability) by synthesizing organic-inorganic-hybrid perovskite or inorganic metal halide perovskite into nanocrystal particles instead of forming a polycrystalline thin film in order to prevent thermal ionization, delocalization of charge carriers, and quenching of excitons.

Also, to solve the problems in which, as the existing colloidal inorganic quantum dot is reduced to a size less than a Bohr exciton diameter (e.g. MAPbBr$_3$~10 nm), it is difficult to adjust the size, and also, color purity and spectrum are affected by the size, and efficiency is reduced due to defects of a nanocrystal surface, the present invention provides colloidal perovskite nanocrystal particles having maximum luminescence efficiency at a size larger than the Bohr exciton diameter, which is not affected by an quantum confinement effect.

Furthermore, the present invention provides nanocrystal particles having more improved luminescence efficiency by synthesizing doped organic-inorganic-hybrid perovskite or inorganic metal halide perovskite into nanocrystal and optoelectronic device using the same.

Furthermore, the present invention provides nanocrystal particles that are capable of being applied for various electronic devices because of being dispersible in all organic solvents.

Technical Solution

To achieve the objectives, one aspect of the present invention provides a perovskite nanocrystal particle. The colloidal perovskite nanocrystal particle is capable of being dispersible in an organic solvent and includes a perovskite nanocrystal structure. The perovskite is an organic-inorganic-hybrid perovskite or an inorganic metal halide perovskite, and the perovskite nanocrystal particle has a diameter greater than a Bohr exciton diameter so that the color spectrum and color purity (Full width at half maximum) are not affected by a quantum confinement effect.

A light-emitter of the perovskite nanocrystal particle may have a diameter of 10 nm to 30 nm.

Here, the organic solvent may be the polar solvent or the non-polar solvent. For example, the polar (aprotic or protic) solvent may include dimethylformamide, gamma butyrolactone, N-methylpyrrolidone, dimethylsulfoxide or isopropyl alcohol, and the non-polar solvent may include dichloroethylene, trichlorethylene, chloroform, chlorobenzene, dichlorobenzene, styrene, xylene, toluene, or cyclohexene.

The perovskite nanocrystal particle may be used as a light-emitter. The light-emitter may have a particle size of 2 nm to 900 nm. In more detail, the light-emitter may have a particle size of 10 nm to 30 nm.

The perovskite nanocrystal particle may be used as a light-emitter. The light-emitter may have an emission wavelength of 200 nm to 1300 nm.

The perovskite nanocrystal particle may have a spherical, cylindrical, cylindroid, polyprism, or two-dimensional (lamellar, plate) shape.

The perovskite nanocrystal particle may have bandgap energy determined by the perovskite crystal structure unlike the inorganic quantum dot light-emitters that depend on the particle size.

However, when the perovskite nanocrystal particle has a size less than a Bohr exciton diameter of the perovskite, the bandgap energy of the nanocrystal particle may be affected by the particle size. Thus, the emission wavelength may be affected by the particle size.

The perovskite nanocrystal particle may have bandgap energy of 1 eV to 5 eV.

The organic-inorganic-hybrid perovskite may have a structure of $ABX_3$, $A_2BX_4$, $ABX_4$, or $A_{n-1}B_nX_{3n+1}$ (where n is an integer between 2 to 6), and the A may be an organic ammonium or alkali material, the B may be a metal material, the X may be a halogen element.

The organic ammonium may be amidinium group organic ions (($CH(NH_2)_2$) $C_xH_{2x+1}(CNH_3)$), $(CH_3NH_3)_n$, $((C_xH_{2x+1})_nNH_3)_n(CH_3NH_3)_n$, $R(NH_2)_2$ (R=alkyl), $(C_nH_{2n+1}NH_3)_n$, $CF_3NH_3$, $(CF_3NH_3)_n$, $(C_xF_{2x+1})_nNH_3)_n$ $(CF_3NH_3)_n$, $((C_xF_{2x+1})_n)_nNH_3)_n$, $(C_nF_{2n+1}NH_3)_n)$, or a derivative thereof (where n is an integer equal to or greater than 1, and x is an integer equal to or greater than 1), the alkali metal material may be Na, K, Rb, Cs, or Fr, or a combination thereof. The B may be a divalent transition metal, an organic material, an ammonium, a rare earth metal, an alkali earth metal, Pb, Sn, Ge, Ga, In, Al, Sb, Bi, Po, or a combination thereof, and the X may be Cl, Br, I, or a combination thereof.

The perovskite nanocrystal particle may further include a plurality of organic or inorganic ligands, inorganic binary compounds or combination thereof surrounding a surface of the perovskite nanocrystal particle.

Each of the organic ligands may include alkyl halide, amines or a carboxylic acid.

An alkyl structure of the alkyl halide may include acyclic alkyl having a structure of $C_nH_{2n+1}$, primary alcohol, secondary alcohol, tertiary alcohol, alkylamine, p-substituted aniline, phenyl ammonium, or fluorine ammonium, and the carboxylic acid may include a 4,4'-Azobis(4-cyanovaleric acid), an acetic acid, a 5-aminosalicylic acid, an acrylic acid, an L-aspentic acid, a 6-bromohexanoic acid, a bromoacetic acid, a dichloro acetic acid, an ethylenediaminetetraacetic acid, an isobutyric acid, an itaconic acid, a maleic acid, an r-maleimidobutyric acid, an L-malic acid, a 4-Nitrobenzoic acid, a 1-pyrenecarboxylic acid, and an oleic acid.

The perovskite may be a doped perovskite.

The doped perovskite may include a structure of $ABX_3$, $A_2BX_4$, $ABX_4$, or $A_{n-1}B_nX_{3n+1}$ (where n is an integer between 2 to 6), where a portion of the A is substituted with A', a portion of the B is substituted with B', or a portion of the X is substituted with X', and the A and A' may be organic ammonium, and the B and B' are metal materials, and X and X' are halogen elements.

Here, the A and A' may be $(CH_3NH_3)_n$, $((C_xH_{2x+1})_n NH_3)_n(CH_3NH_3)_n$, $R(NH_2)_2$ (R=alkyl), $(C_nH_{2n+1}NH_3)_n$, $CF_3NH_3$, $(CF_3NH_3)_n$, $(C_xF_{2x+1})_nNH_3)_n(CF_3NH_3)_n$, $((C_xF_{2x+1})_nNH_3)_n$, $(C_nF_{2n+1}NH_3)_n$, $(CH(NH_2)_2)$, $C_xH_{2x+1}(CNH_3)$, Cs, Rb, K, or a combination or a derivative thereof (where n is an integer equal to or greater than 1, and x is an integer equal to or greater than 1), each of the B and B' may be a divalent transition metal, an ammonium, a rare earth metal, an alkali earth metal, Pb, Sn, Ge, Ga, In, Al, Sb, Bi, or Po, and the X and X' may be Cl, Br, or I.

Also, a ratio at which a portion of the A is substituted with A', a portion of the B is substituted with B', or a portion of the X is substituted with X' may be 0.1% to 5%.

The nanocrystal particle may have a core-shell structure.

The nanocrystal particle may have a structure with a gradient composition.

To achieve the objectives, another aspect of the prevent invention provides a light emitting device. The light emitting device includes: a first electrode; a second electrode; and a light emitting layer, disposed between the first electrode and the second electrode, including the above-described perovskite nanocrystal particle.

To achieve the objectives, another aspect of the prevent invention provides a solar cell. The solar cell includes: a first electrode; a second electrode; and a photoactive layer disposed between the first electrode and the second electrode and including the above-described perovskite nanocrystal particle.

The light emitting layer and the photoactive layer may be manufactured through various solution coating methods such as spin-coating, dip coating, shear coating, bar coating, slot-die coating, inkjet printing, nozzle printing, electrohydrodynamic jet printing, and spray coating.

Advantageous Effects

The perovskite nanocrystal structure having the crystal structure, in which the FCC and the BCC are combined with each other, may be formed in the organic-inorganic-hybrid perovskite or inorganic metal halide perovskite nanocrystal particles, and the organic (or A site) plane and the inorganic plane may be alternately stacked to form the lamellar structure. Particularly, since the organic ammonium without having the conjugated structure is used as the organic material, the excitons may be confined to the inorganic plane to implement the high color purity.

According to the present invention, the bandgap energy of the organic-inorganic-hybrid perovskite nanocrystal particles or the inorganic metal halide perovskite nanocrystal particles may be determined by the perovskite crystal structure, unlike that the bandgap energy of inorganic quantum dot light-emitter depends on the particle size. Thus, since the particle size is greater than the range of the quantum confinement effect, the emission color may not be changed or slightly changed according to the particle size.

Also, the exciton diffusion length may be reduced, and the exciton binding energy may increase in the nanocrystal particle having a size of 10 nm to 30 nm to prevent the excitons from being annihilated by thermal ionization and the delocalization of the charge carriers, thereby luminescence efficiency at room temperature is improved.

Also, the organic-inorganic-hybrid perovskite nanocrystal particles or the inorganic metal halide perovskite nanocrystal particles may be nanoparticles that are dispersible in the organic solvent and thus applied to the various optoelectronic devices.

Also, the organic-inorganic-hybrid perovskite nanocrystal particles or the inorganic metal halide perovskite nanocrystal particles may be doped to increase the luminescence efficiency and the durability (or stability) as well as convert the semiconductor type into the n-type or the p-type, and thereby to adjust the opto-electrical properties.

The effects of the present invention are not limited to the aforementioned effects, but other objects not described herein will be clearly understood by those skilled in the art from descriptions below.

BRIEF DESCRIPTION OF THE DRAWINGS

FIG. 4 is a schematic view illustrating an organic-inorganic-hybrid perovskite nanocrystal particle having a core-shell structure and an energy band diagram of the particle according to an embodiment the present invention.

FIG. 7 is a schematic view illustrating the organic-inorganic-hybrid perovskite nanocrystal particle having the gradient composition structure and an energy band diagram of the particle according to an embodiment of the present invention.

FIG. 10 is a schematic view of a light-emitter according to Manufacturing Example 30 and Comparative Example 1.

MODE FOR CARRYING OUT THE INVENTION

Hereinafter, embodiments of the present invention will be described in detail with reference to the accompanying drawings.

It will be apparent to those skilled in the art that various modifications and variations can be made in the present invention without departing from the spirit or scope of the invention. Thus, it is intended that the present invention covers the modifications and variations of this invention provided they come within the scope of the appended claims and their equivalents.

In the following description, it will be understood that when an element such as a layer, a region, or substrate is referred to as being 'on' another layer, region, or substrate, it can be directly on the other layer, region, or substrate, or intervening layers, regions, or substrates may also be present.

Although the terms such as "first," "second," etc., are used to describe various element, components, regions, layers, and/or portions, it is obvious that the elements, components, regions, layers, and/or portions should not be defined by these terms.

The perovskite nanocrystal particle according to an embodiment of the present invention will be described.

The perovskite nanocrystal particle according to an embodiment of the present invention may include a perovskite nanocrystal structure that is dispersible in an organic solvent. Here, the perovskite may be organic-inorganic-hybrid perovskite or inorganic metal halide perovskite.

Figure 1:
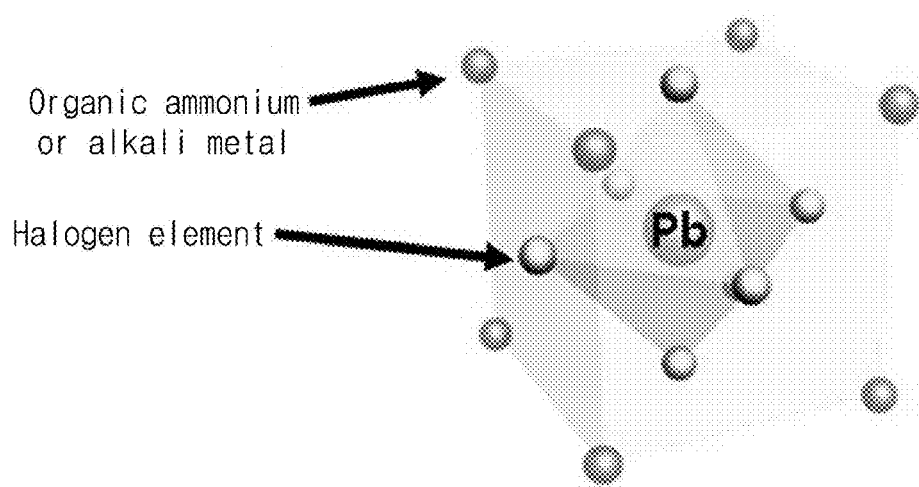
FIG. 1 is a schematic view of a perovskite nanocrystal structure according to an embodiment of the present invention.

FIG. 1 is a schematic view of a perovskite nanocrystal structure according to an embodiment of the present invention.

FIG. 1 illustrates structures of an organic-inorganic-hybrid perovskite nanocrystal and an inorganic metal halide perovskite nanocrystal.

Referring to FIG. 1, the organic-inorganic-hybrid perovskite nanocrystal has a structure with a center metal centered in a face centered cubic (FCC), in which six inorganic halide materials X are respectively located on all surfaces of a hexahedron, and in a body centered cubic (BCC), in which eight organic ammonium OA or inorganic cation are respectively located at all vertexes of a hexahedron. Here, Pb is illustrated as an example of the center metal.

Also, the inorganic metal halide perovskite nanocrystal has structure with a center metal centered in a face centered cubic (FCC), in which six inorganic halide materials X are respectively located on all surfaces of a hexahedron, and in a body centered cubic (BCC), in which eight alkali metals are respectively located at all vertexes of a hexahedron. Here, Pb is illustrated as an example of the center metal.

Here, all sides of the hexahedron have an angle of 90° with respect to each other. The above-described structure may include a cubic structure having the same length in horizontal, vertical, and height directions and a tetragonal structure having different lengths in the horizontal, vertical, and height directions.

Thus, a two-dimensional (2D) structure according to the present invention may be the organic-inorganic-hybrid perovskite nanocrystal structure with a center metal centered in a face centered cubic, in which six inorganic halide materials X are respectively located on all surfaces of a hexahedron, and in a body centered cubic, in which eight organic ammonium or inorganic cations are respectively located at all vertexes of a hexahedron and be defined as a structure of which a horizontal length and a vertical length are the same, but a height length is longer by 1.5 times or more than each of the horizontal length and the vertical length.

Figure 2:
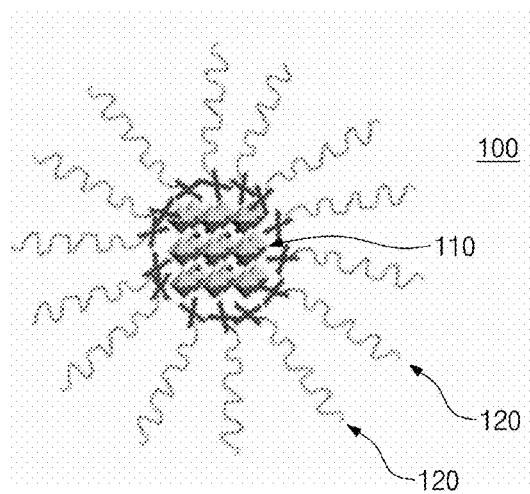
FIG. 2 is a schematic view of an organic-inorganic-hybrid perovskite nanocrystal colloidal particle light-emitter and an inorganic metal halide perovskite nanocrystal particle light-emitter according to an embodiment of the present invention.

FIG. 2 is a schematic view of an organic-inorganic-hybrid perovskite nanocrystal particle light-emitter and an inorganic metal halide perovskite nanocrystal particle light-emitter according to an embodiment of the present invention.

FIG. 2 illustrates the inorganic metal halide perovskite nanocrystal particle light-emitter. The inorganic metal halide perovskite nanocrystal particle according to an embodiment of the present invention may be the same as the above-described organic-inorganic-hybrid perovskite nanocrystal particle except that the A site is the alkali metal instead of the organic ammonium. Here, the alkali metal material, e.g., the A may be Na, K, Rb, Cs, or Fr.

Thus, the organic-inorganic-hybrid perovskite will be described as an example.

Referring to FIG. 2, the organic-inorganic-hybrid perovskite nanocrystal particle 100 may include an organic-inorganic-hybrid perovskite nanocrystal structure 110 that is dispersible in an organic solvent. Here, the organic solvent may be a polar solvent or a non-polar solvent.

For example, the polar (aprotic or protic) solvent may include dimethylformamide, gamma butyrolactone, N-methylpyrrolidone, dimethylsulfoxide or isopropyl alcohol, and the non-polar solvent may include dichloroethylene, trichlorethylene, chloroform, chlorobenzene, dichlorobenzene, styrene, xylene, toluene, or cyclohexene.

Also, the nanocrystal particle 100 has a spherical, cylindrical, cylindroid, polyprism or two-dimensional (lamellar, plate) shape.

Also, the nanocrystal particle has to have a size greater than a Bohr exciton diameter beyond a quantum confinement effect or a quantum size effect. In detail, the nanocrystal particle has to have a size of 2 nm to 900 nm. More preferably, the nanocrystal particle has a size of 20 nm to about 30 nm. Here, the size of the nanocrystal particle represents a size without considering a size of a ligand that will be described later, i.e., a size of a remaining portion except for the ligand.

For example, when the nanocrystal particle has the spherical shape, the nanocrystal particle may have a diameter of 20 nm to 30 nm.

The present invention is characterized in that the bandgap energy of the nanocrystal particle is determined by a structure of the perovskite crystal, unlike that the inorganic quantum dot light-emitter depends on the particle size according to the quantum confinement effect.

However, if the nanocrystal particle has a size less than the Bohr exciton diameter, e.g., 10 nm, the bandgap may be changed by the particle size. Furthermore, since it is difficult to adjust the distribution of the particle size in the nanocrystal particle having a size less than 10 nm, it is difficult to realize high color purity. Although the Bohr exciton diameter varies according to the structure of the material, the Bohr exciton diameter may generally be 10 nm or more. Thus, when the diameter of particle is less than 10 nm, an emission wavelength may be changed even though the particle has the perovskite structure. However, since a change in emission wavelength depending on the particle size is more finally controlled in the synthesis of the particle and processing, it may be a disadvantage in mass production.

Also, if the nanocrystal particle has a size exceeding 30 nm, luminescence of the exciton does not efficiently occur at room temperature by thermal ionization and delocalization of the charge carrier, and the exciton is separated to free charge carriers and then annihilated, thus the luminescence efficiency may be reduced.

Also, the nanocrystal particle may have bandgap energy of 1 eV to 5 eV.

Thus, since the energy bandgap is determined according to the composition and the crystal structure of the nanocrystal particle, the composition of the nanocrystal particle may be adjusted to emit light having a wavelength of, for example, 200 nm to 1300 nm.

The organic-inorganic-hybrid perovskite material may include a structure of $ABX_3$, $A_2BX_4$, $ABX_4$, or $A_{n-1}B_nX_{3n+1}$ (where n is an integer between 2 to 6), where the A may be organic ammonium, the B may be a metal material, and the X may be a halogen element.

For example, the organic ammonium may be amidinium group organic ions (e.g., formamidinium ($NH_2CH=NH^+$) ions, acetamidinium ($NH_2C(CH)=NH_2^+$) ions, guamidinium ($NHC(NH)=NH^+$) ions, organic ammonium anion $((CH_3NH_3)_n$, $((C_xH_{2x+1})_nNH_3)_n(CH_3NH_3)_n$, $R(NH_2)_2$ (R=alkyl), $(C_nH_{2n+1}NH_3)_n$, $(CF_3NH_3)$, $(CF_3NH_3)_n$, $((C_xF_{2x+1})_nNH_3)_n$, $(CF_3NH_3)_n$, $((C_xF_{2x+})_nNH_3)_n$, $(CH(NH_2)_2)$, $C_xH_{2x+1}(CNH_3)$, $(C_nF_{2n+1}NH_3)_n)$, Cs, Rb, K, or a combination thereof (where n is an integer equal to or greater than 1, and x is an integer equal to or greater than 1).

The B may be a divalent transition metal, a rare earth metal, an organic material, an ammonium, an alkali earth metal, Pb, Sn, Ge, Ga, In, Al, Sb, Bi, Po, or a combination thereof. Here, the rare earth metal may be, for example, Ge, Sn, Pb, Eu, or Yb. Also, alkali earth metal may be, for example, Ca or Sr. Also, the X may be Cl, Br, I, or a combination thereof.

A plurality of organic ligands 120 surrounding the surface of the organic-inorganic-hybrid perovskite nanocrystal particle 110 may be further provided.

Each of the organic ligands may include alkyl halide or a carboxylic acid or an amines.

The alkyl halide may have a structure of alkyl-X. Here, the halogen element corresponding to the X may include Cl, Br, or I. Also, the alkyl structure may include acyclic alkyl having a structure of $C_nH_{2n+1}$, primary alcohol having a structure such as $C_nH_{2n+1}OH$, secondary alcohol, tertiary alcohol, alkylamine having a structure of alkyl-N (e.g., hexadecyl amine, 9-Octadecenylamine 1-Amino-9-octadecene ($C_{19}H_{37}N$)), p-substituted aniline, phenyl ammonium, or fluorine ammonium, but is not limited thereto.

The carboxylic acid may include a 4,4'-Azobis(4-cyanovaleric acid), an acetic acid, a 5-aminosalicylic acid, an acrylic acid, an L-aspentic acid, a 6-bromohexanoic acid, a bromoacetic acid, a dichloro acetic acid, an ethylenediaminetetraacetic acid, an isobutyric acid, an itaconic acid, a maleic acid, an r-maleimidobutyric acid, an L-malic acid, a 4-Nitrobenzoic acid, a 1-pyrenecarboxylic acid, or an oleic acid.

The organic-inorganic-hybrid perovskite nanocrystal particle according to the present invention may provide a nanocrystal particle having various bandgaps according to halogen element substitution.

For example, the nanocrystal particles that have the $CH_3NH_3PbCl_3$ organic-inorganic-hybrid perovskite nanocrystal structure may have bandgap energy of about 3.1 eV. For example, the nanocrystal particles that have the $CH_3NH_3PbBr_3$ organic-inorganic-hybrid perovskite nanocrystal structure may have bandgap energy of about 2.3 eV. For example, the nanocrystal particles that have the $CH_3NH_3PbI_3$ organic-inorganic-hybrid perovskite nanocrystal structure may have bandgap energy of about 1.5 eV.

Also, the organic-inorganic-hybrid perovskite nanocrystal particle according to the present invention may provide a nanocrystal particle having various bandgaps according to organic element substitution.

For example, in the $(C_nH_{2n+1}NH_3)_2PbBr_4$, when n=4, a nanocrystal particle having a bandgap of about 3.5 eV may be provided. Also, when n=5, a nanocrystal particle having a bandgap of about 3.33 eV may be provided. Also, when n=7, a nanocrystal particle having a bandgap of about 3.34 eV may be provided. Also, when n=12, a nanocrystal particle having a bandgap of about 3.52 eV may be provided.

Also, the organic-inorganic-hybrid perovskite nanocrystal particle according to the present invention may provide a nanocrystal particle having various bandgaps according to center metal substitution.

For example, the nanocrystal particles that have the $CH_3NH_3PbI_3$ organic-inorganic-hybrid perovskite nanocrystal structure may have bandgap energy of about 1.5 eV. Also, the nanocrystal particles that have the $CH_3NH_3Sn_{0.3}Pb_{0.7}I$ organic-inorganic-hybrid perovskite nanocrystal structure may have bandgap energy of about 1.31 eV. Also, the nanocrystal particles that have the $CH_3NH_3Sn_{0.5}Pb_{0.5}I_3$ organic-inorganic-hybrid perovskite nanocrystal structure may have bandgap energy of about 1.28 eV. Also, the nanocrystal particles that have the $CH_3NH_3Sn_{0.7}Pb_{0.3}I_3$ organic-inorganic-hybrid perovskite nanocrystal structure may have bandgap energy of about 1.23 eV. Also, the nanocrystal particles that have the $CH_3NH_3Sn_{0.9}Pb_{0.1}I_3$ organic-inorganic-hybrid perovskite nanocrystal structure may have bandgap energy of about 1.18 eV. Also, the nanocrystal particles that have the $CH_3NH_3SnI_3$ organic-inorganic-hybrid perovskite nanocrystal structure may have bandgap energy of about 1.1 eV. Also, the nanocrystal particles that have the $CH_3NH_3Pb_xSn_{1-x}Br_3$ organic-inorganic-hybrid perovskite nanocrystal structure may have bandgap energy of about 1.9 eV to 2.3 eV. Also, the nanocrystal particles that have the $CH_3NH_3Pb_xSn_{1-x}Cl_3$ organic-inorganic-hybrid perovskite nanocrystal structure may have bandgap energy of about 2.7 eV to 3.1 eV.

Figure 3:
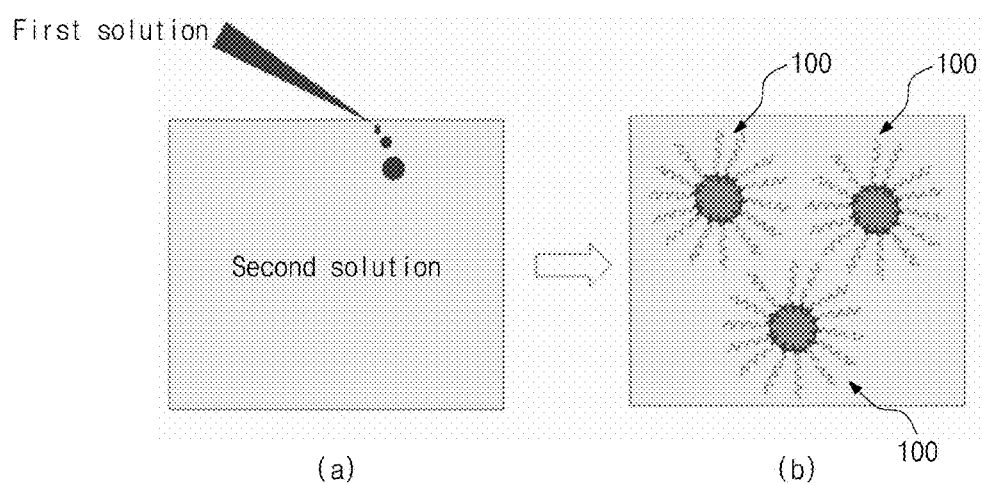
FIG. 3 is a schematic view illustrating a method for manufacturing organic-inorganic-hybrid perovskite nanocrystal colloidal particle according to an embodiment of the present invention.

FIG. 3 is a schematic view illustrating a method for manufacturing the organic-inorganic-hybrid perovskite nanocrystal particle according to an embodiment of the present invention.

Referring to FIG. 3(a), a method for manufacturing the organic-inorganic-hybrid perovskite nanocrystal particle according to an embodiment of the present invention may include a step of preparing a first solution in which organic-inorganic-hybrid perovskite is dissolved in a polar solvent (e.g. dimethylformamidinium) and a second solution in which a surfactant is dissolved in an non-polar (e.g. toluene) solvent and a step of mixing the first solution with the second solution to form nanocrystal particle.

That is, the organic-inorganic-hybrid perovskite nanocrystal particle according to the present invention may be manufactured through an inverse nano-emulsion method, reprecipitation method or hot-injection method.

Hereinafter, more specifically, first, the first solution in which the organic-inorganic-hybrid perovskite is dissolved in the polar solvent and the second solution in which the surfactant is dissolved in an non-polar solvent are prepared.

Here, the polar solvent may include dimethylformamide, gamma butyrolactone, N-methylpyrrolidone, or dimethylsulfoxide, but is not limited thereto.

Also, the organic-inorganic-hybrid perovskite may be a material having a 3D crystal structure or a 2D crystal structure.

For example, the organic-inorganic-hybrid perovskite having the 3D crystal structure may be an $ABX_3$ structure. Also, the organic-inorganic-hybrid perovskite having the 2D crystal structure may be a structure of $ABX_3$, $A_2BX_4$, $ABX_4$, or $A_{n-1}Pb_nX_{3n+1}$ (where, n is an integer between 2 to 6).

Here, the A is an organic ammonium material, the B is a metal material, and the X is a halogen element.

For example, the organic ammonium may be amidinium group organic ions (e.g., formamidinium ($NH_2CH=N^+$) ions, acetamidinium ($NH_2C(CH)=NH_2^+$) ions, guamidinium ($NHC(NH)=N^+$) ions, organic ammonium anion (($CH_3NH_3)_n$, (($C_xH_{2x+1})_nNH_3)_n(CH_3NH_3)_n$, $R(NH_2)_2$ (R=alkyl), $(C_nH_{2n+1}NH_3)_n$, $(CF_3NH_3)$, $(CF_3NH_3)_n$, (($C_xF_{2x+1})_nNH_3)_n(CF_3NH_3)_n$, (($C_xF_{2x+1})_nNH_3)(CH(NH_2)_2)$, $C_xH_{2x+1}(CNH_3)$, $(C_nF_{2n+1}NH_3)_n$, Cs, Rb, K, or a combination or derivative thereof (where n is an integer equal to or greater than 1, and x is an integer equal to or greater than 1).

Also, the B may be a divalent transition metal, an organic material, an inorganic material, an ammonium, a rare earth metal, an alkali earth metal, Pb, Sn, Ge, Ga, In, Al, Sb, Bi, Po, or a combination thereof. Here, the rare earth metal may be, for example, Ge, Sn, Pb, Eu, or Yb. Also, the alkali earth metal may be, for example, Ca, or Sr. Also, the X may be Cl, Br, I, or a combination thereof.

The perovskite may be prepared by combining the AX with $BX_2$ at a predetermined ratio. That is, the first solution may be formed by dissolving the AX and $BX_2$ in the polar solvent at a predetermined ratio. For example, the AX and $BX_2$ may be dissolved in the polar solvent at a ratio of 2:1 to prepare the first solution in which the $A_2BX_4$ organic-inorganic-hybrid perovskite is dissolved.

Also, the polar solvent may include dimethylformamide, gamma butyrolactone, N-methylpyrrolidone, dimethylsulfoxide or isopropyl alcohol, but is not limited thereto.

Also, the surfactant may be an alkyl halide surfactant and have a structure of alkyl-X. Here, the halogen element corresponding to the X may include Cl, Br, or I. Also, the alkyl structure may include acyclic alkyl having a structure of $C_nH_{2n+1}$, primary alcohol having a structure such as $C_nH_{2+1}OH$, secondary alcohol, tertiary alcohol, alkylamine having a structure of alkyl-N (e.g., hexadecyl amine, 9-Octadecenylamine 1-Amino-9-octadecene ($C_{19}H_{37}N$)), p-substituted aniline, phenyl ammonium, or fluorine ammonium) but is not limited thereto.

The surfactant may include an inorganics, amines and carboxylic acid such as a 4,4'-Azobis(4-cyanovaleric acid), an acetic acid, a 5-aminosalicylic acid, an acrylic acid, an L-aspentic acid, a 6-bromohexanoic acid, a bromoacetic acid, a dichloro acetic acid, an ethylenediaminetetraacetic acid, an isobutyric acid, an itaconic acid, a maleic acid, an r-maleimidobutyric acid, an L-malic acid, a 4-Nitrobenzoic acid, a 1-pyrenecarboxylic acid, or an oleic acid, but is not limited thereto.

Next, the first solution may be mixed with the second solution to form the nanocrystal particle.

In the step of mixing the first solution with the second solution to form the nanocrystal particle, it is preferable to mix the first solution by dropping into the second solution drop-wisely. Also, the second solution may be stirred. For example, the first solution in which the organic-inorganic perovskite (OIP) is dissolved may be slowly added drop-wisely into the second solution in which the alkyl halide surfactant that is being strongly stirred is dissolved to synthesize the nanocrystal particle.

In this case, when the first solution drops to be mixed with the second solution, the organic-inorganic perovskite (OIP) is precipitated from the second solution due to a difference in solubility. Also, a surface of the organic-inorganic perovskite (OIP) precipitated from the second solution is surrounded by the alkyl halide surfactant and thus stabilized to generate an organic-inorganic perovskite nanocrystal (OIP-NC) that is well dispersed. Thus, the organic-inorganic-hybrid perovskite nanocrystal particles that have the organic-inorganic perovskite nanocrystal and the plurality of alkyl halide organic ligands or inorganic binary compounds surrounding the organic-inorganic-hybrid perovskite nanocrystal may be manufactured.

The organic-inorganic-hybrid perovskite nanocrystal particle may have a size that is controllable by adjusting a length, a shape factor, and an amount of alkyl halide surfactant. For example, the adjustment of the shape factor may be controlled through the surfactant having a linear, tapered, or inverted triangular shape.

It is preferable that the generated organic-inorganic perovskite nanocrystal has a size of 10 nm to 30 nm in a range equal to or greater than the Bohr exciton diameter beyond the quantum confinement effect. If the organic-inorganic perovskite nanocrystal has a size exceeding 30 nm, it is a fundamental problem in which the large non-radiative decay of the exciton can occur by thermal ionization at room temperature and the delocalization of the charge carrier, and a large number of excitons are separated as the free charge carriers and then annihilated.

Also, in case of the nanocrystal particle having a size less than the Bohr exciton diameter, i.e., 10 nm, the bandgap may be changed by the particle size. In the nanocrystal particle having a size less than 10 nm, it is difficult to adjust the size because the size is reduced, the color purity and the spectrum are not affected by the size, and the efficiency is reduced due to defects of the nanocrystal surface.

The organic-inorganic-hybrid perovskite nanocrystal particle according to an embodiment of the present invention may have a core-shell structure.

Hereinafter, an organic-inorganic-hybrid perovskite nanocrystal particle having a core-shell structure according to an embodiment of the present invention will be described.

FIG. 4 is a schematic view illustrating an organic-inorganic-hybrid perovskite nanocrystal particle having a core-shell structure and an energy band diagram of the particle according to the present invention.

Referring to FIG. 4(a), it is seen that an organic-inorganic-hybrid perovskite nanocrystal particle 100' having a core-shell structure is a structure of a core 115 and a shell 130 surrounding the core 115. Here, a material having a bandgap greater than that of the core 115 may be used as a material of the shell 130.

Referring to FIG. 4(b), since the core 115 has an energy bandgap greater than that of the shell 130, the exciton may be well confined to the core perovskite.

Figure 5:
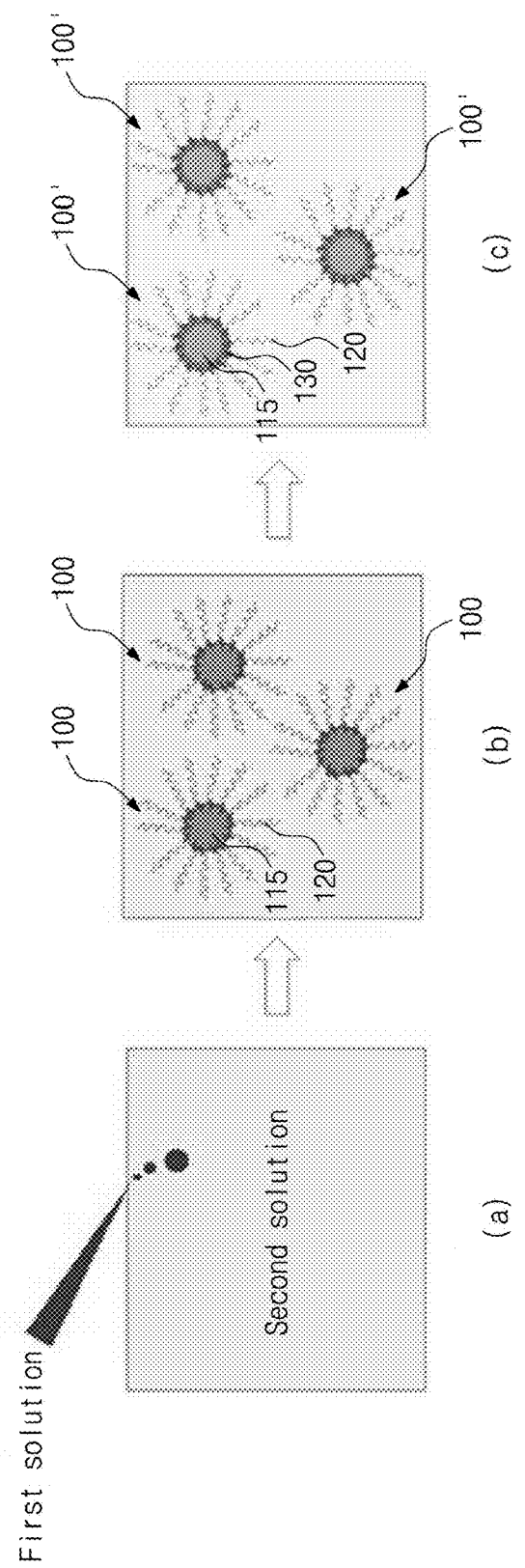
FIG. 5 is a schematic view illustrating a method for manufacturing the organic-inorganic-hybrid perovskite nanocrystal particle having the core-shell structure according to an embodiment of the present invention.

FIG. 5 is a schematic view illustrating a method for manufacturing the organic-inorganic-hybrid perovskite nanocrystal particle having the core-shell structure according to the present invention.

The method for manufacturing the organic-inorganic-hybrid perovskite nanocrystal particle having the core-shell structure may include a step of preparing a first solution in which a first organic-inorganic-hybrid perovskite is dissolved in a polar solvent and a second solution in which an alkyl halide surfactant is dissolved in an non-polar solvent, a step of mixing the first solution with the second solution to form a core that has a first organic-inorganic-hybrid perovskite nanocrystal structure, and a step of forming a shell surrounding the core and that has a material having a bandgap greater than that of the core.

Referring to FIG. 5(a), the first solution in which the organic-inorganic-hybrid perovskite is dissolved in the polar solvent is added drop-wisely into the second solution in which the alkyl halide surfactant is dissolved in the non-polar solvent.

Referring to FIG. 5(b), when the first solution is added to the second solution, the organic-inorganic-hybrid perovskite is precipitated from the second solution due to a difference in solubility. A surface of the precipitated organic-inorganic-hybrid perovskite is surrounded by the alkyl halide surfactant and thus stabilized to generate an organic-inorganic-hybrid perovskite nanocrystal particles 100 that have the organic-inorganic-hybrid perovskite nanocrystal core 115 that is well dispersed. Here, the nanocrystal core 115 is surrounded by the alkyl organic ligands 120.

Since descriptions with reference to FIGS. 5(a) and 5(b) are the same as those with reference to FIG. 3, their detailed descriptions will be omitted.

Referring to FIG. 5(c), the shell 130 surrounding the core 115 and that has the material having the bandgap greater than that of the core 115 may be formed to prepare the organic-inorganic-hybrid perovskite nanocrystal particle 100' having the core-shell structure.

The following five methods may be used to form the shell.

In a first method, the shell may be formed by using a second organic-inorganic-hybrid perovskite solution or an inorganic semiconductor material solution. That is, a third solution in which the second organic-inorganic-hybrid perovskite solution having a bandgap greater than that of the first organic-inorganic-hybrid perovskite or the organic material or the inorganic semiconductor material solution is dissolved may be added to the second solution to form the shell including a second organic-inorganic-hybrid perovskite nanocrystal, an inorganic semiconductor material, an organic polymer or an organic material.

For example, while strongly stirring the organic-inorganic-hybrid perovskite (MAPbBr$_3$) solution generated through the above-described method (the inverse nano-emulsion method, reprecipitation method or hot-injection method), an organic-inorganic-hybrid perovskite (MAPbCl$_3$) solution having a bandgap greater than that of MAPbBr$_3$, an inorganic semiconductor material solution such as ZnS, PbS, and PbSe, a metal oxide (e.g. aluminum oxide, Zn oxide), or an organic polymer such as polyethylene glycol, polyethylene oxide, polyvinylpyrrolidone, polyethyleneimine, and PVA may slowly drop down drop-wisely to form the shell that has the second organic-inorganic-hybrid perovskite nanocrystal (MAPbCl$_3$) or the inorganic semiconductor material. Here, the MA represents methylammonium.

Here, since the core perovskite and the shell perovskite are mixed with each other to form an alloy form or adhere to each other, the organic-inorganic perovskite nanocrystal having the core-shell structure may be synthesized.

Thus, the organic-inorganic-hybrid perovskite nanocrystal particle having the MAPbBr$_3$/MAPbCl$_3$ core-shell structure may be formed.

In a second method, the shell may be formed by using an organic ammonium halide solution. That is, a large amount of organic ammonium halide solution may be added to the second solution and then stirred to form the shell surrounding the core and having a bandgap greater than that of the core.

For example, a MACl solution may be added to the organic-inorganic perovskite (MAPbBr$_3$) solution generated through the above-described method (the inverse nano-emulsion method, reprecipitation method or hot-injection method) and then strongly stirred to convert MAPbBr$_3$ formed on the surface into MAPbBr$_{3-x}$Cl$_x$ by the excess MACl, thereby forming the shell.

Thus, the organic-inorganic-hybrid perovskite nanocrystal particle having the MAPbBr$_3$/MAPbBr$_{3-x}$Cl$_x$ core-shell structure may be formed.

In a third method, the shell may be formed by using a pyrolysis/synthesis method. That is, the second solution may be thermally treated to pyrolyze a surface of the surface, and an organic ammonium halide solution may be added to thermally treated second solution to synthesize the surface again, thereby forming the shell surrounding the core and having a bandgap greater than that of the core.

For example, the organic-inorganic perovskite (MAPbBr$_3$) solution generated through the above-described method (the inverse nano-emulsion method, reprecipitation method or hot-injection method) may be thermally treated to pyrolyze the solution so that a surface is changed into PbBr$_2$, and then, the MACl solution may be added to synthesize the solution so that the surface is changed into MAPbBr$_2$Cl, thereby forming the shell.

Thus, the organic-inorganic-hybrid perovskite nanocrystal particle having the MAPbBr$_3$/MAPbBr$_2$Cl core-shell structure may be formed.

Thus, since the organic-inorganic-hybrid perovskite nanocrystal particle having a core-shell structure formed according to the present invention is formed by using the material having the bandgap greater than that of the core, the exciton may be well confined to the core, and the core perovskite may not be exposed to air by using the perovskite or the organic semiconductor, which is stable in air, to improve durability of the nanocrystal.

In a fourth method, the shell may be formed by using an organic semiconductor material solution. That is, the organic semiconductor material having the bandgap greater than that of the organic-inorganic-hybrid perovskite may be previously dissolved in the second solution, and the first solution, in which the above-described first organic-inorganic-hybrid perovskite is dissolved, may be added to the second solution to form the core that has the first organic-inorganic-hybrid perovskite nanocrystal and the shell that have the organic semiconductor material surrounding the core.

Here, since the organic semiconductor material adheres to the core perovskite surface, the organic-inorganic-hybrid perovskite having the core-shell structure may be synthesized.

Thus, the organic-inorganic-hybrid perovskite nanocrystal light-emitter having the $MAPbBr_3$ core-shell structure may be formed.

In a fifth method, the shell may be formed by using a selective extraction method. That is, a small amount of IPA solution may be added to the second solution in which the core that has the first organic-inorganic-hybrid perovskite nanocrystal is formed to selectively extract MABr from the nanocrystal surface and form the surface by using only $PbBr_2$ to form the shell having a bandgap greater than that of the core.

For example, the small amount of IPA may be added to the organic-inorganic perovskite ($MAPbBr_3$) solution generated through the above-described method (the inverse nano-emulsion method, reprecipitation method, or hot-injection method) to selectively dissolve only the MABr on the nanocrystal surface to extract the MABr so that only the $PbBr_2$ remains on the surface, thereby forming the $PbBr_2$ shell.

That is, the MABr may be removed from the $MAPbBr_3$ surface through the selective extraction.

Thus, the organic-inorganic-hybrid perovskite nanocrystal light emitting body having the $MAPbBr_3$—$PbBr_2$ core-shell structure may be formed.

Figure 6:
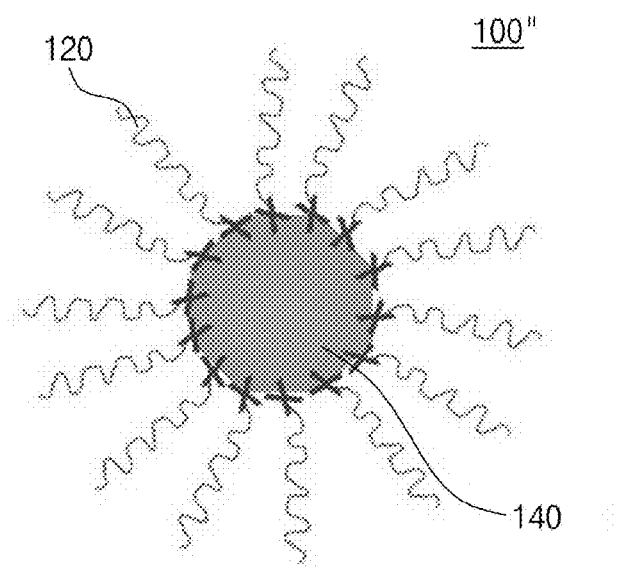
FIG. 6 is a schematic view of an organic-inorganic-hybrid perovskite nanocrystal particle having a gradient composition structure according to an embodiment of the present invention.

FIG. 6 is a schematic view of an organic-inorganic-hybrid perovskite nanocrystal particle having a gradient composition structure according to an embodiment of the present invention.

Referring to FIG. 6, an organic-inorganic-hybrid perovskite nanocrystal particle 100" having a gradient composition according to an embodiment of the present invention includes an organic-inorganic-hybrid perovskite nanocrystal structure 140 that is dispersible in an organic solvent and has a gradient composition structure that is gradually changed in composition outward from a center. Here, the organic solvent may be a polar solvent or a non-polar solvent.

The organic-inorganic-hybrid perovskite may have a structure of $ABX_{3-m}X'_m$, $A_2BX_{4-l}X'_l$, or $ABX_{4-k}X'_k$, the A is an organic ammonium material, the B is a metal material, the X is Br, and the X' is Cl. Also, the m, l, and k values gradually increase outward from a center of the nanocrystal structure 140.

Thus, an energy bandgap may gradually increase outward from the center of the nanocrystal structure 140.

For example, the organic ammonium may be amidinium group organic ions (e.g., formamidinium ($NH_2CH=N^+$) ions, acetamidinium ($NH_2C(CH)=NH_2$) ions, guamidinium ($NHC(NH)=N^+$) ions, organic ammonium anions (($CH_3NH_3$)$_n$, (($C_xH_{2x+1}$)$_n NH_3$)($CH_3NH_3$)$_n$, $R(NH_2)_n$ (R=alkyl), ($C_nH_{2n+1}NH_3$)$_n$, ($CF_3NH_3$), ($CF_3NH_3$)$_n$, (($C_xF_{2x+1}$)$_n NH_3$)$_n$($CF_3NH_3$), (($C_xF_{2x+1}$)$_n NH_3$)$_n$, ($CH(NH_2)_2$), $C_xH_{2x+1}(CNH_3)$, ($C_nF_{2n+1}NH_3$)$_n$, Cs, Rb, K, or a derivative thereof (where n is an integer equal to or greater than 1, and x is an integer equal to or greater than 1).

The B may be a divalent transition metal, an organic material, an ammonium, a rare earth metal, an alkali earth metal, Pb, Sn, Ge, Ga, In, Al, Sb, Bi, Po, or a combination thereof.

Also, the m, l, and k values gradually increase outward from the center of the nanocrystal structure. Thus, the energy bandgap may gradually increase according to a variation in composition.

For another example, the m, l, and k values gradually increase in a stir shape outward from the center of the nanocrystal structure. Thus, the energy bandgap may gradually increase in the stir shape according to a variation in composition.

Also, a plurality of organic ligands or inorganic binary compounds 120 surrounding the organic-inorganic-hybrid perovskite nanocrystal structure 140 may be further provided. Each of the organic ligands 120 may include alkyl halide. The alkyl halide may have a structure of alkyl-X. Here, the halogen element corresponding to the X may include Cl, Br, or I. Also, the alkyl structure may include acyclic alkyl having a structure of $C_nH_{2n+1}$, primary alcohol having a structure such as $C_nH_{2+1}OH$, secondary alcohol, tertiary alcohol, alkylamine having a structure of alkyl-N (e.g., hexadecyl amine, 9-Octadecenylamine 1-Amino-9-octadecene ($C_{19}H_{37}N$)), p-substituted aniline, phenyl ammonium, or fluorine ammonium, but is not limited thereto.

Thus, the nanocrystal structure may be manufactured into a gradient-alloy type to gradually change contents of a large amount of perovskite existing outside the nanocrystal structure and a large amount of perovskite existing inside the nanocrystal structure. Since the content of the perovskite is gradually changed in the nanocrystal structure, a fraction within the nanocrystal structure may be uniformly adjusted, and surface oxidation may be reduced to improve exciton confinement in the large amount of perovskite existing in the nanocrystal structure, thereby improving the luminescence efficiency and durability (or stability).

A method for manufacturing the organic-inorganic-hybrid perovskite nanocrystal particle having the gradient composition structure according to an embodiment of the present invention will be described.

A method for manufacturing the organic-inorganic-hybrid perovskite nanocrystal particle having the gradient composition structure according to an embodiment of the present invention includes a step of preparing an organic-inorganic-hybrid perovskite nanocrystal particle having a core-shell structure and a step of thermally treating the organic-inorganic-hybrid perovskite nanocrystal particle having the core-shell structure to form the organic-inorganic-hybrid perovskite nanocrystal particle having a gradient composition through interdiffusion.

First, the organic-inorganic-hybrid perovskite nanocrystal particle having the core-shell structure may be prepared. Since the method for manufacturing the organic-inorganic-hybrid perovskite nanocrystal particle having the core-shell structure is the same as that with reference to FIG. 5, its detailed description will be omitted.

Then, the organic-inorganic-hybrid perovskite nanocrystal particle having the core-shell structure may be thermally treated to form the organic-inorganic-hybrid perovskite nanocrystal particle having the gradient composition through the interdiffusion.

For example, the organic-inorganic-hybrid perovskite having the core-shell structure may be annealed at a high temperature to form a solid solution state and then be thermally treated to form the organic-inorganic-hybrid perovskite nanocrystal particle having the gradient composition through interdiffusion.

For instance, thermal treatment may be performed at a temperature of 100° C. to 150° C. The organic-inorganic-hybrid perovskite having the core-shell structure may be annealed at the terminal treating temperature to induce the interdiffusion.

A method for manufacturing the organic-inorganic-hybrid perovskite nanocrystal particle having a gradient composition structure according to another embodiment of the present invention includes a step of forming a first organic-inorganic-hybrid perovskite nanocrystal core and a step of forming a second organic-inorganic-hybrid perovskite nanocrystal shell having the gradient composition.

First, the first organic-inorganic-hybrid perovskite nanocrystal core is formed. Since the method for the first organic-inorganic-hybrid perovskite nanocrystal core is the same as that for forming the above-described nanocrystal core, its detailed description will be omitted.

Then, the second organic-inorganic-hybrid perovskite nanocrystal shell having the gradient composition, which surrounds the core, is formed.

The second organic-inorganic-hybrid perovskite may have a structure of $ABX_{3-m}X'_m$, $A_2BX_{4-l}X'_l$, or $ABX_{4-k}X'_k$, the A is an organic ammonium material, the B is a metal material, the X is Br, and the X' is Cl.

Thus, when the m, l, or k value increases in the second solution, a third solution, in which second organic-inorganic-hybrid perovskite is dissolved, may be added.

That is, a solution in which the composition of $ABX_{3-m}X'_m$, $A_2BX_{4-l}X'_l$, or $ABX_{4-k}X'_k$ is controlled may continuously drop down to form the shell that continuously varies in composition.

FIG. 7 is a schematic view illustrating the organic-inorganic-hybrid perovskite nanocrystal particle having the gradient composition structure and an energy band diagram of the particle according to an embodiment of the present invention.

Referring to FIG. 7(a), it is seen that a nanocrystal particle 100" according to the present invention is the organic-inorganic-hybrid perovskite nanocrystal structure having the gradient composition that varies in content. Referring to FIG. 7(b), since the composition of the material is gradually changed outward from a center of the organic-inorganic-hybrid perovskite nanocrystal structure 140, the organic-inorganic-hybrid perovskite nanocrystal particle may be manufactured so that an energy bandgap thereof gradually increases outward from the center.

The perovskite nanocrystal particle according to the present invention may be a doped perovskite nanocrystal particle.

The doped perovskite may include a structure of $ABX_3$, $A_2BX_4$, $ABX_4$, or $A_{n-1}B_nX_{3n+1}$ (where n is an integer between 2 to 6). Here, a portion of the A is substituted with A', a portion of the B is substituted with B', or a portion of the X is substituted with X'. The A and A' may be organic ammonium, and the B and B' may be metal materials, and X and X' may be halogen elements.

Here, the A and A', i.e.,

The organic ammonium may be amidinium group organic ions $(C_xH_{2x+1}(C(NH_2)_2))$ (e.g., formamidinium $(NH_2CH=NH^+)$ ions, acetamidinium $(NH_2C(CH)=NH_{2+})$ ions, guamidinium $(NHC(NH)=NH^+)$ ions, organic ammonium anion $((CH_3NH_3)_n$, $((C_xH_{2x+1})_nNH_3)_n(CH_3NH_3)_n$, $R(NH_2)_2$ (R=alkyl), $(C_nH_{2n+1}NH_3)_n$, $(CF_3NH_3)$, $(CF_3NH_3)_n$, $((C_xF_{2x+1})_nNH_3)_n(CF_3NH_3)$, $((C_xF_{2x+1})_nNH_3)_n$, $(CH(NH_2)_2)$, $(C_nF_{2n+1}NH_3)_n$, Cs, Rb, K, or derivative thereof (where n is an integer equal to or greater than 1, and x is an integer equal to or greater than 1). Each of B and B' may be a divalent transition metal, an organics, an inorganics, an ammonium, a rare earth metal, an alkali earth metal, Pb, Sn, Ge, Ga, In, Al, Sb, Bi, or Po, and the X and X' may be Cl, Br, or I.

Also, a ratio at which a portion of the A is substituted with A', a portion of the B is substituted with B', or a portion of the X is substituted with X' may be 0.1% to 5%.

Figure 8:
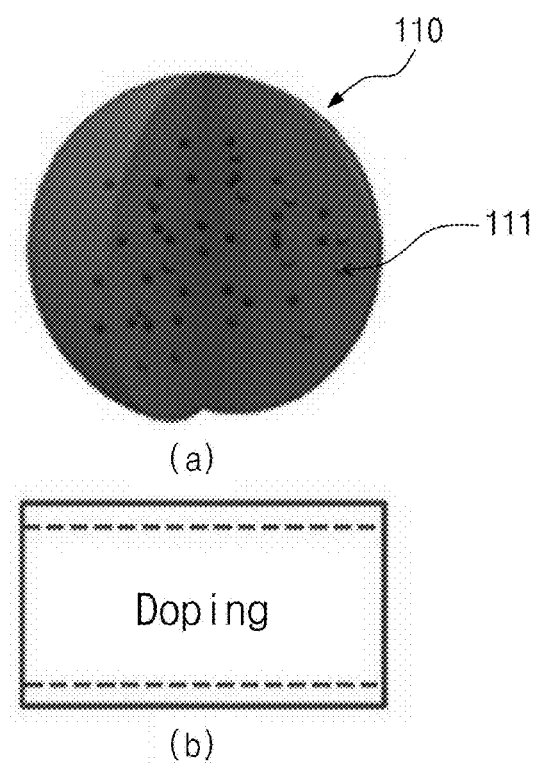
FIG. 8 is a schematic view of an organic-inorganic-hybrid perovskite nanocrystal particle having a gradient composition structure according to an embodiment of the present invention.

FIG. 8 is a schematic view of a doped perovskite nanocrystal particle and an energy band diagram of the particle according to an embodiment of the present invention.

FIG. 8(a) is a partially cut-away view of an organic-inorganic-hybrid perovskite nanocrystal structure into which a doping element 111 is doped. FIG. 8(b) is a band diagram of the doped organic-inorganic-hybrid perovskite nanocrystal structure 110.

Referring to FIGS. 8(a) and 8(b), a semiconductor type of the organic-inorganic-hybrid perovskite may be converted into an n-type or a p-type through the doping. For example, when Cl is partially doped into a MAPbI$_3$ organic-inorganic-hybrid perovskite nanocrystal, the semiconductor type may be converted into the n-type to adjust an optoelectronic property. Here, the MA is methylammonium.

The doped organic-inorganic-hybrid perovskite nanocrystal particle according to an embodiment of the present invention will be described. A method for manufacturing the organic-inorganic-hybrid perovskite nanocrystal particle through an inverse nano-emulsion, reprecipitation method or hot-injection method will be described as an example.

First, the first solution in which the doped organic-inorganic-hybrid perovskite is dissolved in the polar solvent is added drop-wisely into the second solution in which the alkyl halide surfactant is dissolved in the non-polar solvent.

Here, the polar solvent may include dimethylformamide, gamma butyrolactone, N-methylpyrrolidone, dimethylsulfoxide or iso-propyl alcohol, but is not limited thereto.

Here, the doped organic-inorganic-hybrid perovskite may include a structure of $ABX_3$, $A_2BX_4$, $ABX_4$, or $A_{n-1}B_nX_{3n+1}$. Also, a portion of the A is substituted with A', a portion of the B is substituted with B', or a portion of the X is substituted with X'.

Here, the A and A' may be organic ammonium, the B and B' may be metal materials or an organic material, and the X and X' may be halogen elements. For example, the A may be $(CH_3NH_3)_n$, $((CH_{2x+1})_nNH_3)_n(CH_3NH_3)_n$, $R(NH_2)_2$ (R=alkyl), $(C_nH_{2n+1}NH_3)_n$, $(CF_3NH_3)$, $(CF_3NH_3)_n$, $((C_xF_{2x+1})_nNH_3)(CF_3NH_3)_n$, $((C_xF_{2x+1})_nNH_3)_n$, $(CH(NH_2)_2)$, $CH_{2x+1}(CNH_3)$, Cs, Rb, K, $(C_nF_{2n+1}NH_3)_n$ or combination or derivative thereof. Also, each of the B and B' may be a divalent transition metal, an organic material, an ammonium, a rare earth metal, an alkali earth metal, Pb, Sn, Ge, Ga, In, Al, Sb, Bi, or Po. Here, the rare earth metal may be, for example, Ge, Sn, Pb, Eu, or Yb. Also, alkali earth metal may be, for example, Ca or Sr. Also, each of the X and X' may be Cl, Br, or I.

Also, the A and A' may be organic materials different from each other, the B and B' may be metals different from each other, and the X and X' may be halogen elements different from each other. Furthermore, it is preferable that an element that is not alloyed with the X is used as the doped X'.

For example, $CH_3NH_3I$, $PbI_2$, and $PbCl_2$ may be added to a DMF solution to form a first solution. Here, a molar ratio of $CH_3NH_3I$:$PbI_2$ and $PbCl_2$ may be set to 1:1, and a molar ratio of $PbI_2$:$PbCl_2$ may be set to 97:3.

When the A is $CH_3NH_3$, and the X is Br as an example of the AX synthesis, $CH_3NH_2$ (methylamine) and HBr (hydroiodic acid) may be dissolved under a nitrogen atmosphere to obtain $CH_3NH_3Br$ through evaporation of the solvent.

Then, when the first solution is added to the second solution, the doped organic-inorganic-hybrid perovskite is precipitated from the second solution due to a difference in solubility. A surface of the precipitated doped organic-inorganic-hybrid perovskite is surrounded by the alkyl halide surfactant and thus stabilized to generate a doped organic-inorganic-hybrid perovskite nanocrystal particles 100 that have the doped organic-inorganic-hybrid perovskite nanocrystal structure that is well dispersed. Here, the surface of the doped organic-inorganic-hybrid perovskite nanocrystal particle is surrounded by organic ligands that are alkyl halide.

Thereafter, a solution including the doped organic-inorganic-hybrid perovskite nanocrystal particle that is dispersed in a non-polar solvent, in which the alkyl halide surfactant is dissolved, may be heated and thus selectively evaporated, or a co-solvent, in which all the polar and non-polar solvents are capable of being dissolved, may be added to selectively extract the polar solvent including the nanocrystal particle from the non-polar solvent, thereby obtaining the doped organic-inorganic-hybrid perovskite nanocrystal particle.

The organic-inorganic-hybrid perovskite nanocrystal particle and the inorganic metal halide perovskite nanocrystal particle according to an embodiment of the present invention may be applied to various optoelectronic devices.

For example, the organic-inorganic-hybrid perovskite nanocrystal particle and the inorganic metal halide perovskite nanocrystal particle may be applied to a light emitting device by using a light emitting layer including the above-described organic-inorganic-hybrid perovskite nanocrystal particle and the inorganic metal halide perovskite nanocrystal particle. The light emitting device may be disposed on a first electrode and a second electrode and between the first and second electrodes and include the light emitting layer including the above-described perovskite nanocrystal particle.

For another example, the organic-inorganic-hybrid perovskite nanocrystal particle and the inorganic metal halide perovskite nanocrystal particle may be applied to a solar cell by using a photoactive layer including the above-described organic-inorganic-hybrid perovskite nanocrystal particle and the inorganic metal halide perovskite nanocrystal particle. The solar cell may include a first electrode, a second electrode, and a photoactive layer disposed between the first electrode and the second electrode and including the above-described perovskite nanocrystal particle.

Manufacturing Example 1

An organic-inorganic-hybrid perovskite nanocrystal particle having a 3D structure according to an embodiment of the present invention was formed. The organic-inorganic-hybrid perovskite nanocrystal particle was formed through an inverse nano-emulsion method, reprecipitation method or hot-injection method.

Particularly, organic-inorganic-hybrid perovskite was dissolved in a polar solvent to prepare a first solution. Here, dimethylformamide was used as the polar solvent, and $CH_3NH_3PbBr_3$ was used as the organic-inorganic-hybrid perovskite. Here, the used $CH_3NH_3PbBr_3$ was prepared by mixing $CH_3NH_3Br$ with $PbBr_2$ at a ratio of 1:1.

Also, a second solution in which an alkyl halide surfactant is dissolved in a non-polar solvent was prepared. Here, toluene was used as the non-polar solvent, and octadecylammonium bromide ($CH_3(CH_2)_{17}NH_3Br$) was used as the alkyl halide surfactant.

Then, the first solution slowly dropped drop-wisely into the second solution that is being strongly stirred to form the organic-inorganic-hybrid perovskite nanocrystal particle having the 3D structure.

Then, the organic-inorganic-hybrid perovskite nanocrystal particle that is in a liquid state was spin-coated on a glass substrate to form an organic-inorganic-hybrid perovskite nanocrystal particle thin film (OIP-NP film).

Here, the formed organic-inorganic-hybrid perovskite nanocrystal particle has a size of about 10-30 nm.

Manufacturing Example 2

The same process as that according to Manufacturing Example 1 was performed, and $CH_3(CH_2)_{13}NH_3Br$ was used as an alkyl halide surfactant to form an organic-inorganic-hybrid perovskite nanocrystal particle having a 3D structure according to an embodiment of the present invention.

Here, the formed organic-inorganic-hybrid perovskite nanocrystal particle has a size of about 30 nm on average.

Manufacturing Example 3

The same process as that according to Manufacturing Example 1 was performed, and $CH_3(CH_2)_{10}NH_3Br$ was used as an alkyl halide surfactant to form an organic-inorganic-hybrid perovskite nanocrystal particle having a 3D structure according to an embodiment of the present invention.

Here, the formed organic-inorganic-hybrid perovskite nanocrystal particle has a size of about 40 nm on average.

Manufacturing Example 4

The same process as that according to Manufacturing Example 1 was performed, and $CH_3(CH_2)_7NH_3Br$ was used as an alkyl halide surfactant to form an organic-inorganic-hybrid perovskite nanocrystal particle having a 3D structure according to an embodiment of the present invention.

Here, the formed organic-inorganic-hybrid perovskite nanocrystal particle has a size of about 50 nm on average.

Manufacturing Example 5

The same process as that according to Manufacturing Example 1 was performed, and $CH_3(CH_2)_4NH_3Br$ was used as an alkyl halide surfactant to form an organic-inorganic-hybrid perovskite nanocrystal particle having a 3D structure according to an embodiment of the present invention.

Here, the formed organic-inorganic-hybrid perovskite nanocrystal particle has a size of about 70 nm on average.

Manufacturing Example 6

The same process as that according to Manufacturing Example 1 was performed, and $CH_3CH_2NH_3Br$ was used as an alkyl halide surfactant to form an organic-inorganic-hybrid perovskite nanocrystal particle having a 3D structure according to an embodiment of the present invention.

Here, the formed organic-inorganic-hybrid perovskite nanocrystal particle has a size of about 80 nm on average.

Manufacturing Example 7

The same process as that according to Manufacturing Example 1 was performed, and $CH_3NH_3Br$ was used as an alkyl halide surfactant to form an organic-inorganic-hybrid perovskite nanocrystal particle having a 3D structure according to an embodiment of the present invention.

Here, the formed organic-inorganic-hybrid perovskite nanocrystal particle has a size of about 100 nm on average.

Manufacturing Example 8

The organic-inorganic-hybrid perovskite nanocrystal according to Manufacturing Example 1 is used as a core. Also, a second organic hybrid perovskite ($MAPbCl_3$) solution having a large bandgap slowly dropped drop wise into a solution containing the organic-inorganic-hybrid perovskite nanocrystal core to form a shell including a second organic-inorganic-hybrid perovskite nanocrystal ($MAPbCl_3$), thereby forming an organic-inorganic-hybrid perovskite nanocrystal particle having a 3D core-shell structure according to an embodiment of the present invention.

Manufacturing Example 9

The organic-inorganic-hybrid perovskite nanocrystal according to Manufacturing Example 2 is used as a core. Also, a second organic hybrid perovskite ($MAPbCl_3$) solution having a large bandgap slowly dropped drop-wisely into a solution containing the organic-inorganic-hybrid perovskite nanocrystal core to form a shell including a second organic-inorganic-hybrid perovskite nanocrystal ($MAPbCl_3$), thereby forming an organic-inorganic-hybrid perovskite nanocrystal particle having a 3D core-shell structure according to an embodiment of the present invention.

Manufacturing Example 10

The organic-inorganic-hybrid perovskite nanocrystal according to Manufacturing Example 3 is used as a core. Also, a second organic hybrid perovskite ($MAPbCl_3$) solution having a large bandgap slowly dropped drop-wisely into a solution containing the organic-inorganic-hybrid perovskite nanocrystal core to form a shell including a second organic-inorganic-hybrid perovskite nanocrystal ($MAPbCl_3$), thereby forming an organic-inorganic-hybrid perovskite nanocrystal particle having a 3D core-shell structure according to an embodiment of the present invention.

Manufacturing Example 11

The organic-inorganic-hybrid perovskite nanocrystal according to Manufacturing Example 4 is used as a core. Also, a second organic hybrid perovskite ($MAPbCl_3$) solution having a large bandgap slowly dropped drop-wisely into a solution containing the organic-inorganic-hybrid perovskite nanocrystal core to form a shell including a second organic-inorganic-hybrid perovskite nanocrystal ($MAPbCl_3$), thereby forming an organic-inorganic-hybrid perovskite nanocrystal particle having a 3D core-shell structure according to an embodiment of the present invention.

Manufacturing Example 12

The organic-inorganic-hybrid perovskite nanocrystal according to Manufacturing Example 5 is used as a core. Also, a second organic hybrid perovskite ($MAPbCl_3$) solution having a large bandgap slowly dropped drop-wisely into a solution containing the organic-inorganic-hybrid perovskite nanocrystal core to form a shell including a second organic-inorganic-hybrid perovskite nanocrystal ($MAPbCl_3$), thereby forming an organic-inorganic-hybrid perovskite nanocrystal particle having a 3D core-shell structure according to an embodiment of the present invention.

Manufacturing Example 13

The organic-inorganic-hybrid perovskite nanocrystal according to Manufacturing Example 6 is used as a core. Also, a second organic hybrid perovskite ($MAPbCl_3$) solution having a large bandgap slowly dropped drop-wisely into a solution containing the organic-inorganic-hybrid perovskite nanocrystal core to form a shell including a second organic-inorganic-hybrid perovskite nanocrystal ($MAPbCl_3$), thereby forming an organic-inorganic-hybrid perovskite nanocrystal particle having a 3D core-shell structure according to an embodiment of the present invention.

Manufacturing Example 14

The organic-inorganic-hybrid perovskite nanocrystal according to Manufacturing Example 7 is used as a core. Also, a second organic hybrid perovskite ($MAPbCl_3$) solution having a large bandgap slowly dropped drop-wisely into a solution containing the organic-inorganic-hybrid perovskite nanocrystal core to form a shell including a second organic-inorganic-hybrid perovskite nanocrystal ($MAPbCl_3$), thereby forming an organic-inorganic-hybrid perovskite nanocrystal particle having a 3D core-shell structure according to an embodiment of the present invention.

Manufacturing Example 15

The same process as that according to Manufacturing Example 8 was performed, and $(CH_3NH_3)_2PbBr4$ was used as the core organic-inorganic-hybrid perovskite. Here, the used $(CH_3NH_3)_2PbBr4$ was prepared by mixing $CH_3NH_3Br$ with $PbBr_2$ at a ratio of 2:1.

Here, the formed organic-inorganic-hybrid perovskite nanocrystal particle having the core-shell shape emits light near to an ultraviolet or blue color. The luminescence spectrum is located at about 380 nm.

Manufacturing Example 16

The same process as that according to Manufacturing Example 8 was performed, and $(CH_3NH_3)_2PbI_4$ was used as the core organic-inorganic-hybrid perovskite. Here, the used $(CH_3NH_3)_2PbI_4$ was prepared by mixing $CH_3NH_3I$ with $PbI2$ at a ratio of 2:1.

Here, the formed organic-inorganic-hybrid perovskite nanocrystal particle having the core-shell shape emits light near to an ultraviolet or red color. The luminescence spectrum is located at about 780 nm.

Manufacturing Example 17

The same process as that according to Manufacturing Example 8 was performed, and $(CH_3NH_3)_2PbCl_xBr_{4-x}$ was used as the core organic-inorganic-hybrid perovskite. Here, the used $(CH_3NH_3)_2PbCl_xBr_{4-x}$ was prepared by mixing $CH_3NH_3Cl$ with $PbBr_2$ at a predetermined ratio.

Here, the luminescence spectrum of the formed organic-inorganic-hybrid perovskite nanocrystal particle having the core-shell shape is located between 380 nm and 520 nm.

Manufacturing Example 18

The same process as that according to Manufacturing Example 8 was performed, and $(CH_3NH_3)_2PbI_xBr_{4-x}$ was used as the core organic-inorganic-hybrid perovskite. Here, the used $(CH_3NH_3)_2PbI_xBr_{4-x}$ was prepared by mixing $CH_3NH_3I$ with $PbBr_2$ at a predetermined ratio.

Here, the luminescence spectrum of the formed organic-inorganic-hybrid perovskite nanocrystal particle having the core-shell shape is located between 520 nm and 780 nm.

Manufacturing Example 19

The same process as that according to Manufacturing Example 8 was performed, and $(CH(NH2)_2)_2PbI_4$ was used as the core organic-inorganic-hybrid perovskite. Here, the used $(CH(NH2)_2)_2PbI_4$ was prepared by mixing $CH(NH2)_2I$ with $PbI2$ at a ratio of 2:1.

Here, the luminescence spectrum of the formed organic-inorganic-hybrid perovskite nanocrystal particle having the core-shell shape emits infrared light and is located at about 800 nm.

Manufacturing Example 20

The same process as that according to Manufacturing Example 8 was performed, and $(CH_3NH_3)_2Pb_xSn_{1-x}I_4$ was used as the core organic-inorganic-hybrid perovskite. Here, the used $(CH_3NH_3)_2Pb_xSn_{1-x}I_4$ was prepared by mixing $CH_3NH_3I$ with $Pb_xSn_{1-x}I_2$ at a ratio of 2:1.

Here, the luminescence spectrum of the formed organic-inorganic-hybrid perovskite nanocrystal particle having the core-shell shape is located between 820 nm and 1120 nm.

Manufacturing Example 21

The same process as that according to Manufacturing Example 8 was performed, and $(CH_3NH_3)_2Pb_xSn_{1-x}Br_4$ was used as the core organic-inorganic-hybrid perovskite. Here, the used $(CH_3NH_3)_2Pb_xSn_{1-x}Br_4$ was prepared by mixing $CH_3NH_3Br$ with $Pb_xSn_{1-x}Br_2$ at a ratio of 2:1.

Here, the luminescence spectrum of the formed organic-inorganic-hybrid perovskite nanocrystal particle having the core-shell shape is located between 540 nm and 650 nm.

Manufacturing Example 22

The same process as that according to Manufacturing Example 8 was performed, and $(CH_3NH_3)_2Pb_xSn_{1-x}Cl_4$ was used as the core organic-inorganic-hybrid perovskite. Here, the used $(CH_3NH_3)_2Pb_xSn_{1-x}Cl_4$ was prepared by mixing $CH_3NH_3Cl$ with $Pb_xSn_{1-x}Cl_2$ at a ratio of 2:1.

Here, the luminescence spectrum of the formed organic-inorganic-hybrid perovskite nanocrystal particle having the core-shell shape is located between 400 nm and 460 nm.

Manufacturing Example 23

The same process as that according to Manufacturing Example 8 was performed, and $(C_4H_9NH_3)PbBr_4$ was used as the core organic-inorganic-hybrid perovskite. Here, the used $(C_4H_9NH_3)PbBr_4$ was prepared by mixing $(C_4H_9NH_3)Br$ with $PbBr_2$ at a ratio of 2:1.

Here, the luminescence spectrum of the formed organic-inorganic-hybrid perovskite nanocrystal particle having the core-shall shape is located at about 411 nm.

Manufacturing Example 24

The same process as that according to Manufacturing Example 8 was performed, and $(C_5H_{11}NH_3)PbBr_4$ was used as the core organic-inorganic-hybrid perovskite. Here, the used $(C_5H_{11}NH_3)PbBr_4$ was prepared by mixing $(C_5H_{11}NH_3)Br$ with $PbBr_2$ at a ratio of 2:1.

Here, the luminescence spectrum of the formed organic-inorganic-hybrid perovskite nanocrystal particle having the core-shall shape is located at about 405 nm.

Manufacturing Example 25

The same process as that according to Manufacturing Example 8 was performed, and $(C_7H_{15}NH_3)PbBr_4$ was used as the core organic-inorganic-hybrid perovskite. Here, the used $(C_7H_{15}NH_3)PbBr_4$ was prepared by mixing $(C_7H_{15}NH_3)Br$ with $PbBr_2$ at a ratio of 2:1.

Here, the luminescence spectrum of the formed core-shell organic-inorganic-hybrid perovskite nanocrystal particle is located at about 401 nm.

Manufacturing Example 26

The same process as that according to Manufacturing Example 8 was performed, and $(C_{12}H_{25}NH_3)PbBr_4$ was used as the core organic-inorganic-hybrid perovskite. Here, the used $(C_{12}H_{25}NH_3)PbBr_4$ was prepared by mixing $(C_{12}H_{25}NH_3)Br$ with $PbBr_2$ at a ratio of 2:1.

Here, the luminescence spectrum of the formed organic-inorganic-hybrid perovskite nanocrystal particle having the core-shall shape is located at about 388 nm.

Manufacturing Example 27

The doped organic-inorganic-hybrid perovskite nanocrystal particle according to an embodiment of the present invention was formed. The organic-inorganic-hybrid perovskite nanocrystal particle was formed through an inverse nano-emulsion method, reprecipitation method or hot-injection method.

Particularly, the doped organic-inorganic-hybrid perovskite was dissolved in a polar solvent to prepare a first solution. Here, dimethylformamide was used as the polar solvent, and $CH_3NH_3PbI_3$, into which Cl is doped, was used as the organic-inorganic-hybrid perovskite. Here, the used $CH_3NH_3PbI_3$, into which Cl is doped, was prepared by mixing $CH_3NH_3I$:$PbI_2$ at a ratio of 1:1. Also, $PbBr_2$:$PbC_2$ was mixed at a ratio of 97:3. Thus, a first solution in which 3% Cl-doped $CH_3NH_3PbI_3$ is dissolved was prepared.

Also, a second solution in which an alkyl halide surfactant is dissolved in a non-polar solvent was prepared.

Here, toluene was used as the non-polar solvent, and $CH_3(CH_2)_{17}NH_3I$ was used as the alkyl halide surfactant.

Then, the first solution slowly dropped drop-wisely into the second solution that is being strongly stirred to form a nanocrystal particle including the Cl-doped organic-inorganic-hybrid perovskite nanocrystal structure.

Then, the organic-inorganic-hybrid perovskite nanocrystal particle that is in a liquid state was spin-coated on a glass substrate to form an organic-inorganic-hybrid perovskite nanocrystal particle thin film (OIP-NP film).

Manufacturing Example 28

An inorganic metal halide perovskite nanocrystal particle having a 3D structure according to an embodiment of the present invention was formed. The inorganic metal halide perovskite nanocrystal particle was formed through an inverse nano-emulsion method, reprecipitation method or hot-injection method.

Particularly, $Cs_2CO_3$ and an oleic acid were added to octadecene (ODE) that is a non-polar solvent to react at a high temperature, thereby preparing a third solution. $PbBr_2$, the oleic acid, and oleylamine were added to the non-polar solvent to react for one hour at a high temperature (120° C.), thereby preparing a fourth solution. Then, the third solution slowly dropped drop wise into the fourth solution that is being strongly stirred to form the inorganic metal halide perovskite nanocrystal particle having the 3D structure.

Then, the inorganic metal halide perovskite nanocrystal particle that is in a liquid state was spin-coated on a glass substrate to form an inorganic metal halide perovskite nanocrystal particle thin film.

Here, the formed inorganic metal halide perovskite nanocrystal particle has a size of about 10-30 nm.

Manufacturing Example 29

The inorganic metal halide perovskite ($CsPbBr_3$) nanocrystal according to Manufacturing Example 28 is used as a core. Also, a second inorganic metal halide perovskite ($CsPbCl_3$) solution having a large bandgap slowly dropped drop-wisely into a solution containing the inorganic metal halide perovskite nanocrystal core to form a shell including a second inorganic metal halide perovskite nanocrystal ($CsPbCl_3$), thereby forming an inorganic metal halide perovskite nanocrystal particle having a core-shell structure according to an embodiment of the present invention.

Manufacturing Example 30

The same process as that according to Manufacturing Example 1 except that the oleic acid ($CH_3 (CH_2)_7CH=CH (CH_2)_7COOH$) is used as an surfactant was performed to form an organic-inorganic-hybrid perovskite nanocrystal particle having a 3D structure.

Here, an amount of oleic acid was adjusted to adjust a size of the organic-inorganic-hybrid perovskite nanocrystal particle.

Manufacturing Example 31

A light emitting device according to an embodiment of the present invention was manufactured.

First, after an ITO substrate (a glass substrate coated with an ITO anode) is performed, PEDOT:PSS (AI4083 from Heraeus company) that is a conductive material was spin-coated on the ITO anode and then thermally treated for 30 minutes at a temperature of 150° C. to form a hole injection layer having a thickness of 40 nm.

The solution in which the organic-inorganic-hybrid perovskite nanocrystal particle manufactured according to Manufacturing Example 1 is dissolved was spin-coated on the hole injection layer and then thermally treated for 20 minutes at a temperature of 80° C. to form an organic-inorganic-hybrid perovskite nanocrystal particle light emitting layer.

Thereafter, 1,3,5-Tris(1-phenyl-1H-benzimidazol-2-yl) benzene (TPBI) having a thickness of 50 nm was deposited on the organic-inorganic-hybrid perovskite nanocrystal particle light emitting layer under a high vacuum state of $1 \times 10^{-7}$ Torr or more to form an electron transport layer, and then, LiF having a thickness of 1 nm was deposited on the electron transport layer to form an electron injection layer. Then, aluminum having a thickness of 100 nm was deposited on the electron injection layer to form a cathode, thereby manufacturing an organic-inorganic-hybrid perovskite nanocrystal particle light emitting device.

Manufacturing Example 32

A solar cell according to an embodiment of the present invention was manufactured.

First, after an ITO substrate (a glass substrate coated with an ITO anode) is performed, PEDOT:PSS (AI4083 from CLEVIOS PH company) that is a conductive material was spin-coated on the ITO anode and then thermally treated for 30 minutes at a temperature of 150° C. to form a hole extraction layer having a thickness of 40 nm.

The organic-inorganic-hybrid perovskite nanocrystal colloidal particle manufactured according to Manufacturing Example 1 was mixed with Phenyl-C61-butyric acid methyl ester (PCBM) and then applied to the hole extraction layer to form a photoactive layer, and Al having a thickness of 100 nm was deposited on the photoactive layer to manufacture a perovskite nanocrystal colloidal particle solar cell.

Comparative Example 1

$CH_3NH_3PbBr_3$ was dissolved in dimethylformamide that is a polar solvent to manufacture a first solution.

Then, the first solution was spin-coated on a glass substrate to manufacture a $CH_3NH_3PbBr_3$ thin film (OIP film).

Comparative Example 2

$CH_3NH_3PbCl_3$ was dissolved in dimethylformamide that is a polar solvent to manufacture a first solution.

Then, the first solution was spin-coated on a glass substrate to manufacture a $CH_3NH_3PbCl_3$ thin film (OIP film).

Experimental Example

Figure 9:
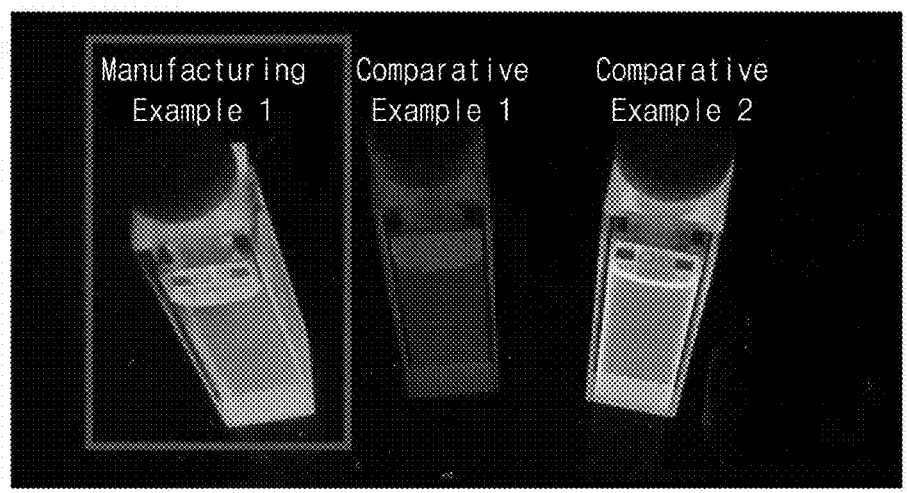
FIG. 9 is a fluorescent image obtained by photographing emission light by irradiating ultraviolet rays onto a light-emitter according to Manufacturing Example 1, Comparative Example 1, and Comparative Example 2.

FIG. 9 is a fluorescent image obtained by photographing emission light by irradiating ultraviolet rays onto a light-emitter according to Preparation Example 1, Comparative Example 1, and Comparative Example 2.

Referring to FIG. 9, it is seen that an organic-inorganic-hybrid perovskite solution, which is not in the form of a nanocrystal particle, but in the form of a bulk, according to Comparative Example 1 and Comparative Example 2 emits dark light, but the light-emitter having the nanocrystal particle according to Manufacturing Example 1 emits very bright green light.

On the other hand, in Comparative Example 1 and Comparative Example 2, the organic-inorganic-hybrid perovskite having the form of the thin film, which is manufactured by spin-coating on the glass substrate, had a PLQY value of about 1%.

FIG. 10 is a schematic view of a light-emitter according to Manufacturing Example 1 and Comparative Example 1.

FIG. 10(a) is a schematic view of a nano thin film according to Comparative Example 1, FIG. 7(b) is a schematic view of a nanocrystal particle thin film according to Manufacturing Example 1. Referring to FIG. 7(a), the nanocrystal particle according to Comparative Example 1 has the form of the thin film manufactured by spin-coating the first solution on the glass substrate. Referring to FIG. 7(b), the nanocrystal particle according to Manufacturing Example 1 has the form of the nanocrystal structure 110.

Figure 11:
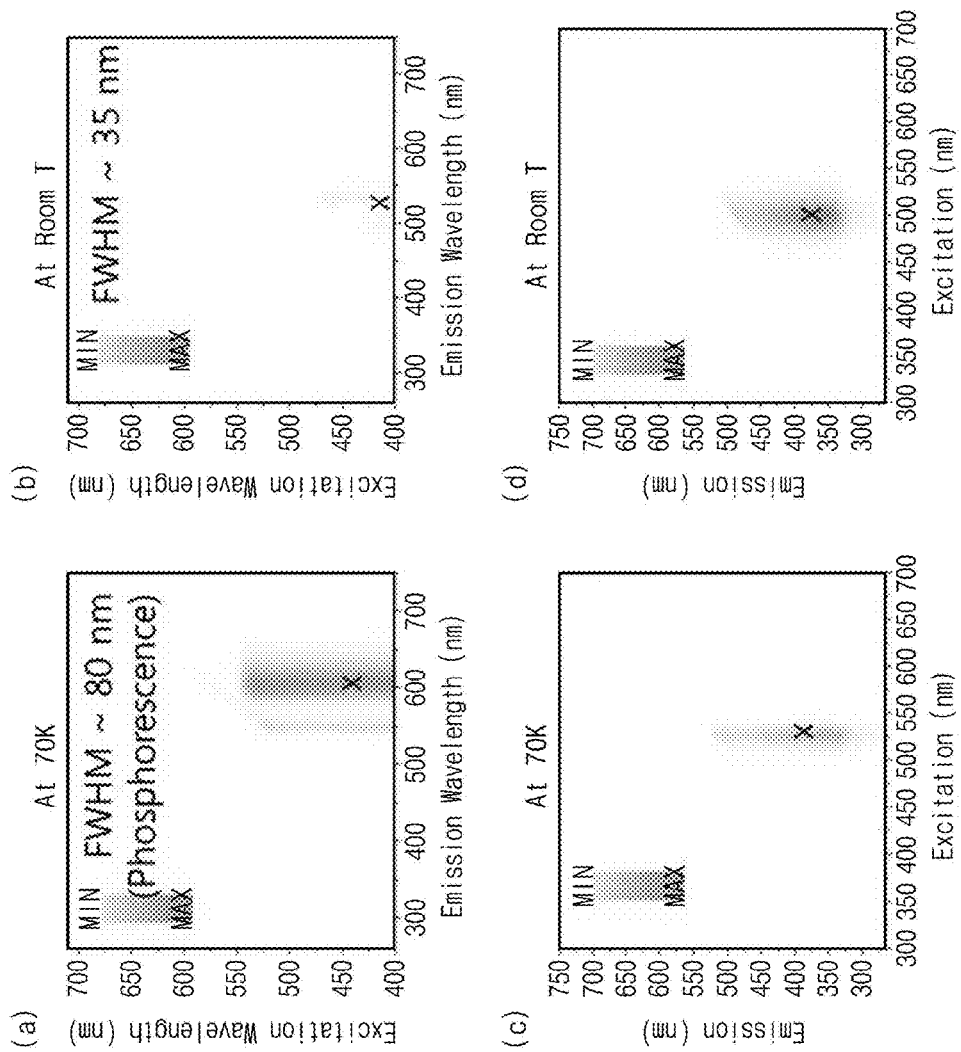
FIG. 11 is an image obtained by photographing a photoluminescence matrix of the light-emitter at room temperature and a low temperature according to Manufacturing Example 30 and Comparative Example 1.

FIG. 11 is an image obtained by photographing a photoluminescence matrix of the light-emitter at room temperature and a low temperature according to Manufacturing Example 1 and Comparative Example 1.

FIG. 11(a) is an image obtained by photographing a photoluminescence matrix of the thin film-shaped organic-inorganic-hybrid perovskite (OIP film) according to Comparative Example 1 at a low temperature (70K), and FIG. 10(b) is an image obtained by photographing a photoluminescence matrix of the thin film-shaped organic-inorganic-hybrid perovskite (OIP film) according to Comparative Example 1 at room temperature.

FIG. 11(c) is an image obtained by photographing a photoluminescence matrix of the organic-inorganic-hybrid perovskite nanocrystal particle thin film (OIP-NP film) according to Manufacturing Example 1 at a low temperature (70K), and FIG. 11(d) is an image obtained by photographing a photoluminescence matrix of the organic-inorganic-hybrid perovskite nanocrystal particle (OIP-NP film) according to Manufacturing Example 1 at room temperature.

Referring to FIGS. 11(a) and 11(d), in case of the organic-inorganic-hybrid perovskite nanocrystal particle thin film (OIP-NP film) according to Manufacturing Example 1, it is seen that photoluminescence occurs at the same position as that of the thin film-shaped organic-inorganic-hybrid perovskite (OIP film) according to Comparative Example 1, and color purity is more improved. Also, in case of the OIP-NP film according to Manufacturing Example 1, it is seen that photoluminescence having high color purity occurs at room temperature at the same position as that at the low temperature, and intensity of the luminescence is not reduced. On the other hand, the organic-inorganic-hybrid perovskite according to Comparative Example 1 has different color purity and luminescence position at room temperature and low temperature, and exciton does not efficiently emit light due to thermal ionization and delocalization of charge carriers at room temperature and thus is separated as free charge carriers and annihilated to cause low luminescence intensity.

Figure 12:
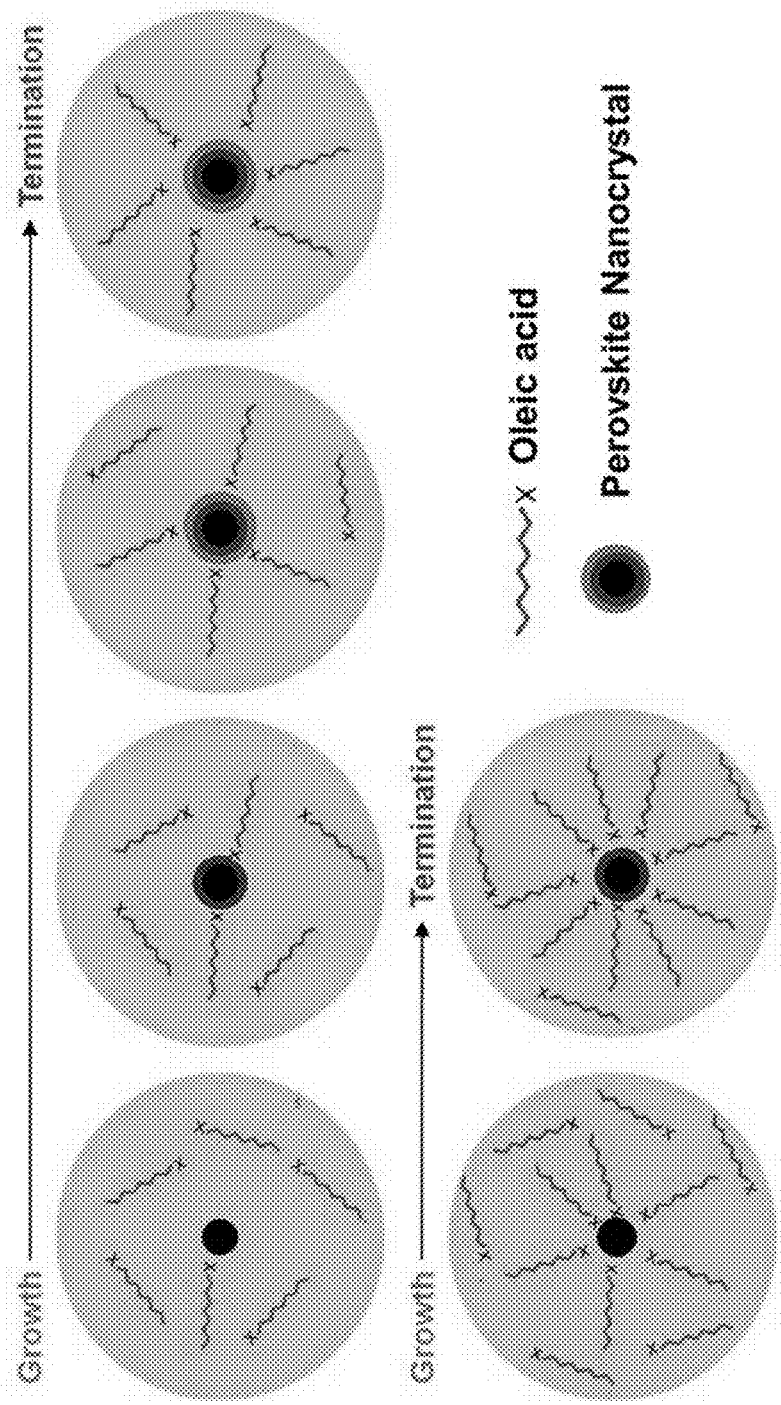
FIG. 12 is a schematic view illustrating synthesis of a nanocrystal that is adjustable in size according to an amount of surfactant.

FIG. 12 is a schematic diagram of a nanocrystal that is adjustable in size according to an amount of surfactant.

Referring to FIG. 12, when an amount of oleic acid that is a surfactant is small, it is seen that a rate of crystallization from growth to termination of the perovskite nanocrystal is slow. On the other hand, when an amount of surfactant is large, it is seen that a rate of the crystallization increases to form the perovskite nanocrystal having a smaller size.

Figure 13:
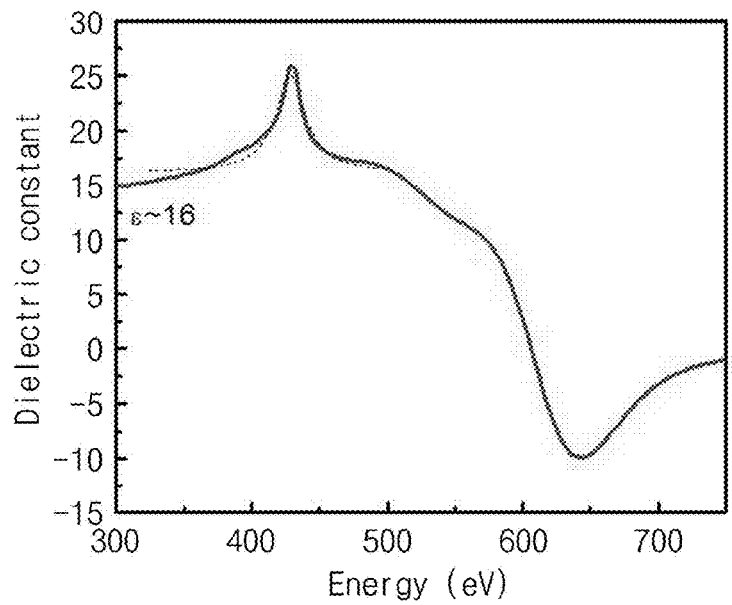
FIG. 13 is data obtained by measuring a dielectric constant of the organic-inorganic-hybrid perovskite.

FIG. 13 is data obtained by measuring a dielectric constant of the organic-inorganic-hybrid perovskite ($CH_3NH_3PbBr_3$). The perovskite has a dielectric constant of about 16. Also, a Bohr exciton diameter may be measured through an effective mass of the perovskite and the following Equation 1.

$$r = a_0 \varepsilon_r \frac{m_0}{\mu} \quad <\text{Equation 1}>$$

(where r is a Bohr exciton diameter, $a_0$ is a Bohr exciton diameter (0.053 nm) of hydrogen, $\varepsilon_r$ is a dielectric constant, $\mu = m_e \times m_h/(m_e + m_h)$ $m_e$ is an effective electron mass, and $m_h$ is an effective hole mass).

Figure 14:
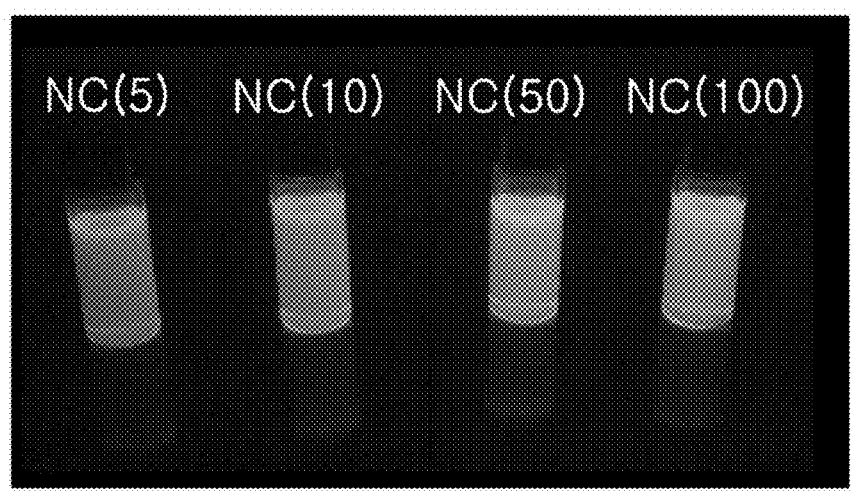
FIG. 14 is an emission image of a nanocrystal having various sizes, which is synthesized by changing an amount of surfactant.

FIG. 14 is an emission image of a nanocrystal having various sizes, which is synthesized by changing an amount of surfactant. NC(1.5), NC(2), NC(5), NC(10), NC(50), and NC(100), which are illustrated in FIGS. 14 to 24 have a nanocrystal diameter of 100 nm, 50 nm, 35 nm, 20 nm, 7 nm, and 3 nm, respectively. Here, the number in each of parentheses is a μl unit as an amount of surfactant. Thus, the more an amount of surfactant increases, the more a size of the nanocrystal decreases.

Referring to FIG. 14, it is seen that light having a shorter wavelength is emitted when an amount of surfactant increases to reduce a size of the perovskite nanocrystal particle.

Figure 15:
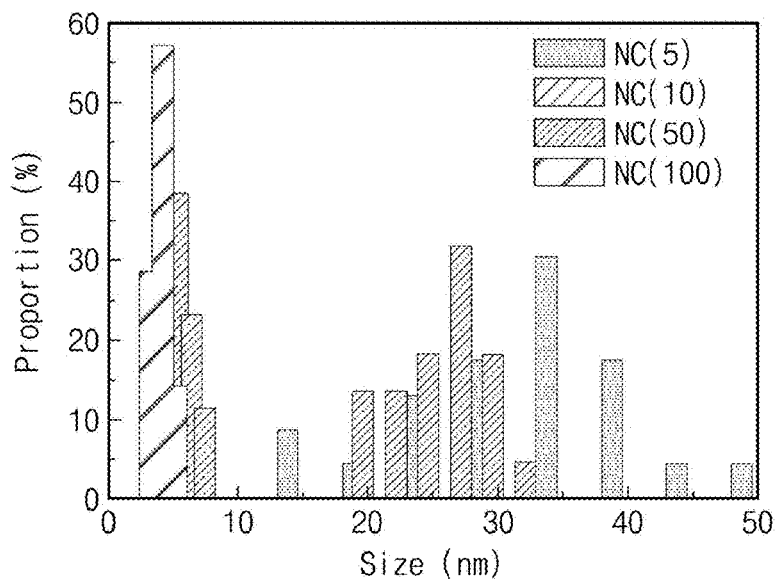
FIG. 15 is data displaying a variation in size by adjusting an amount of surfactant according to Manufacturing Example 30.

FIG. 15 is data displaying a variation in size by adjusting an amount of surfactant according to Manufacturing Example 1.

Referring to FIG. 15, when manufactured according to Manufacturing Example 1, it is seen that a rate of crystallization increases by increasing an amount of surfactant used to stabilize the organic-inorganic-hybrid perovskite in a solution phase, and thus, the perovskite nanocrystal particle gradually decreases in size.

Figure 16:
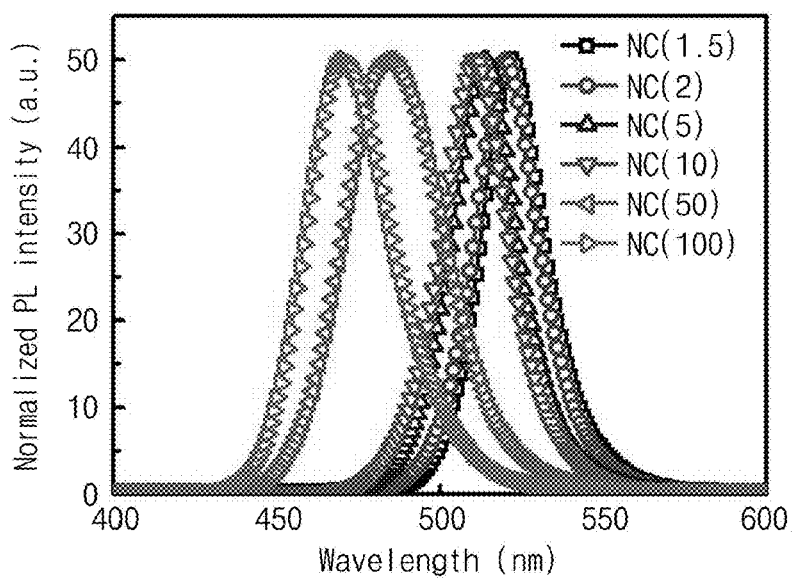
FIG. 16 is data of photoluminescence in which a size varies by adjusting an amount of surfactant according to Manufacturing Example 30.

FIG. 16 is data of photoluminescence in which a size varies by adjusting an amount of surfactant according to Manufacturing Example 1.

Referring to FIG. 16, it is seen that a photoluminescence spectrum has a short wavelength when an amount of surfactant increases, and the nanocrystal particle gradually decreases in size. This is done due to a quantum confinement effect caused by the nanocrystal size being smaller than that of the Bohr exciton diameter when the amount of surfactant increases to a predetermined amount or more.

Figure 17:
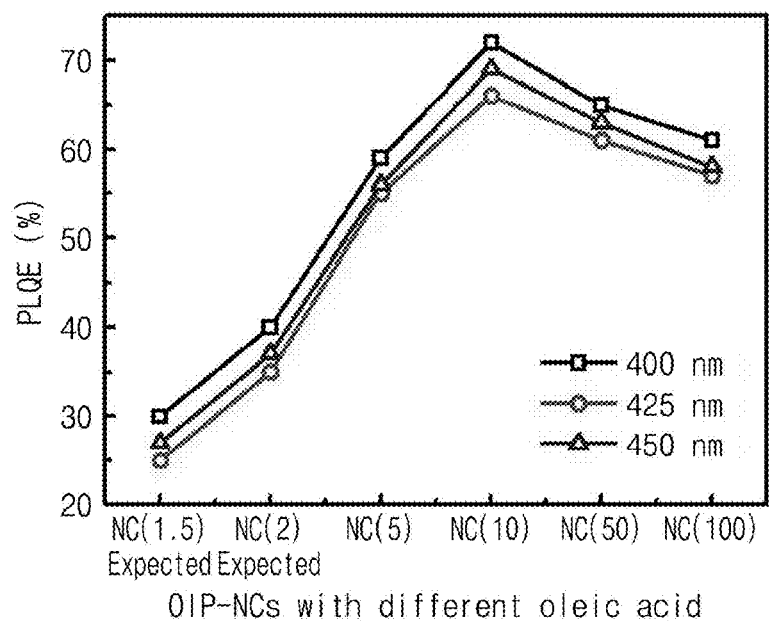
FIG. 17 is a view illustrating photoluminescence quantum efficiency depending on a size according to Manufacturing Example 30.

FIG. 17 is a view illustrating photoluminescence quantum efficiency depending on a size according to Manufacturing Example 1.

Referring to FIG. 17, it is seen that the photoluminescence quantum efficiency is the highest at the organic-inorganic-hybrid perovskite nanocrystal having a particle size (NC (10)), which is near to or greater than the Bohr exciton diameter just before the quantum confinement effect occurs. When the nanocrystal has a size greater than the Bohr exciton diameter, since the exciton has small exciton binding energy, the exciton does not emit light at room temperature due to thermal ionization and delocalization of a charge carrier and thus is separated as the free charge carriers and then annihilated. Also, when the nanocrystal has a size less than the Bohr exciton diameter, the luminescence efficiency may be reduced by defects occurring on the nanocrystal particle surface.

The photoluminescence quantum efficiency (PLQE), the emission wavelength, the emission full width at half maximum (FWHM) according to the size of the perovskite nanocrystal are summarized in Table 1.

TABLE 1

| Nanocrystal size (nm) | Luminescence efficiency (PLQE) (%) | Emission wavelength (Wavelength) (nm) | Full width at half maximum (FWHM) (nm) |
|---|---|---|---|
| 3 | 63 | 470 | 30 |
| 7 | 66 | 502 | 35 |

TABLE 1-continued

| Nanocrystal size (nm) | Luminescence efficiency (PLQE) (%) | Emission wavelength (Wavelength) (nm) | Full width at half maximum (FWHM) (nm) |
|---|---|---|---|
| 20 | 72 | 511 | 26 |
| 35 | 60 | 514 | 23 |
| 50 | 40 | 520 | 21 |
| 100 | 30 | 520 | 21 |

Figure 18:
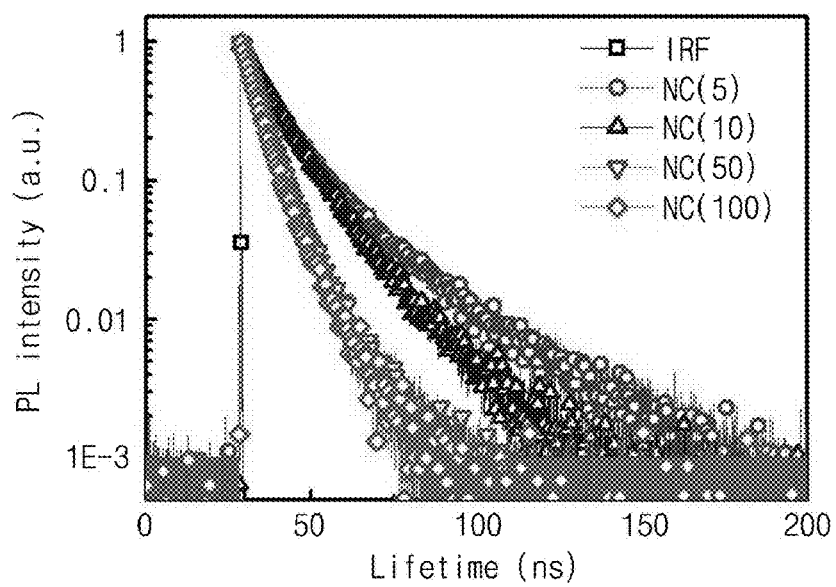
FIG. 18 is data obtained by analyzing an exciton lifetime depending on a size according to Manufacturing Example 30.

FIG. 18 is data obtained by analyzing an exciton lifetime depending on a size according to Manufacturing Example 1.

Referring to FIG. 18, it is seen that the exciton lifetime decreases as the size of the organic-inorganic-hybrid perovskite nanocrystal particle decreases. Here, as the size of the nanocrystal particle decreases, the exciton binding energy increases. As a result, the exciton may be annihilated in an exciton state without being separated into free charge carriers and thus shortened in lifetime.

Figure 19:
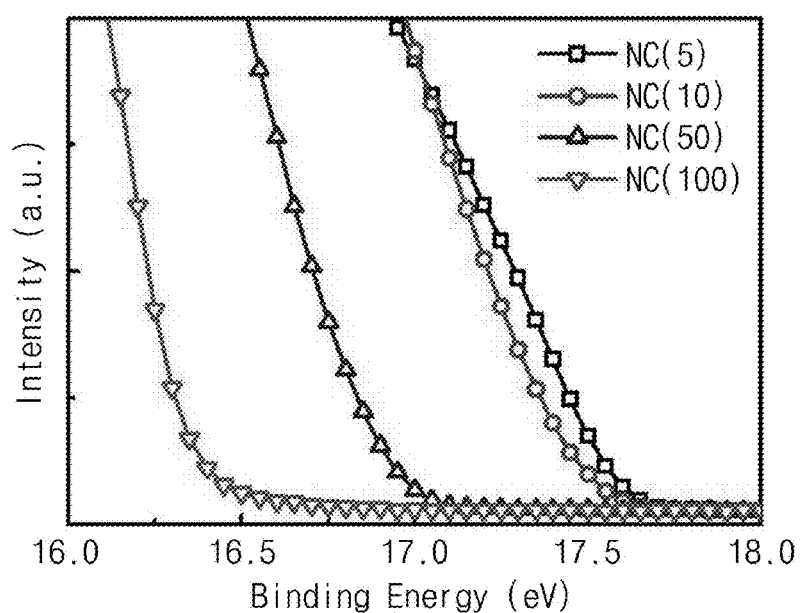
FIG. 19 is data obtained by measuring ionization potential energy of a perovskite nanocrystal depending on a size according to Manufacturing Example 30.

FIG. 19 is data obtained by measuring ionization potential energy of a perovskite nanocrystal depending on a size according to Manufacturing Example 1.

Referring to FIG. 19, it is seen that the quantum confinement effect occurs as the size of the nanocrystal particle becomes smaller than the Bohr exciton diameter, and thus, the ionization potential gradually becomes deeper.

Figure 20:
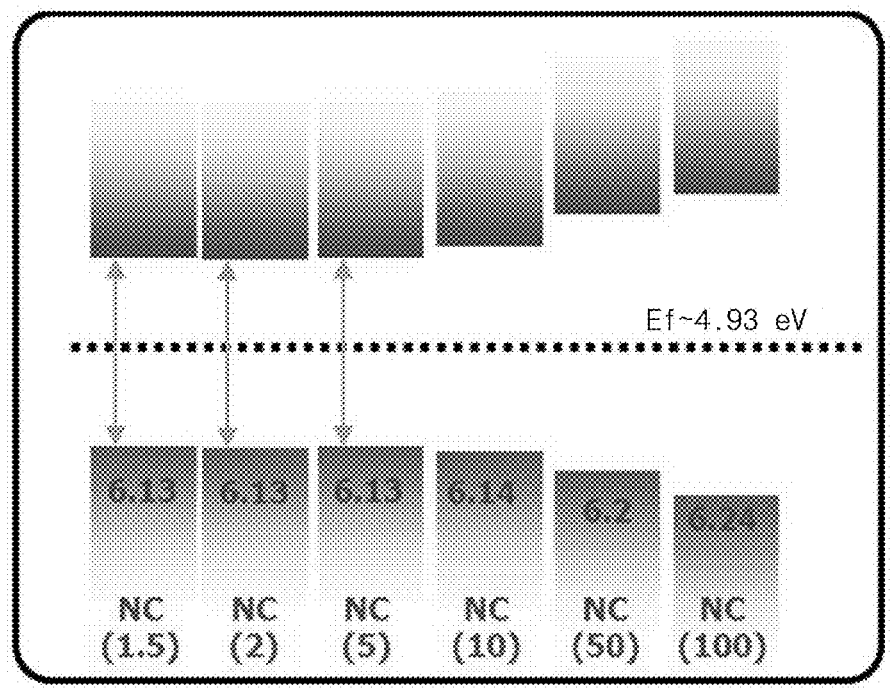
FIG. 20 is a schematic diagram illustrating an energy distribution of the perovskite nanocrystal depending on a size according to Manufacturing Example 1.

FIG. 20 is a schematic diagram illustrating an energy distribution of the perovskite nanocrystal depending on a size according to Manufacturing Example 1.

FIG. 20 is a view of an energy level depending on a size of the nanocrystal. Referring to FIG. 19, it is seen that the ionization potential gradually becomes deeper, and electron affinity energy gradually become shallower to increase a bandgap as the size of the nanocrystal particle decreases.

Figure 21:
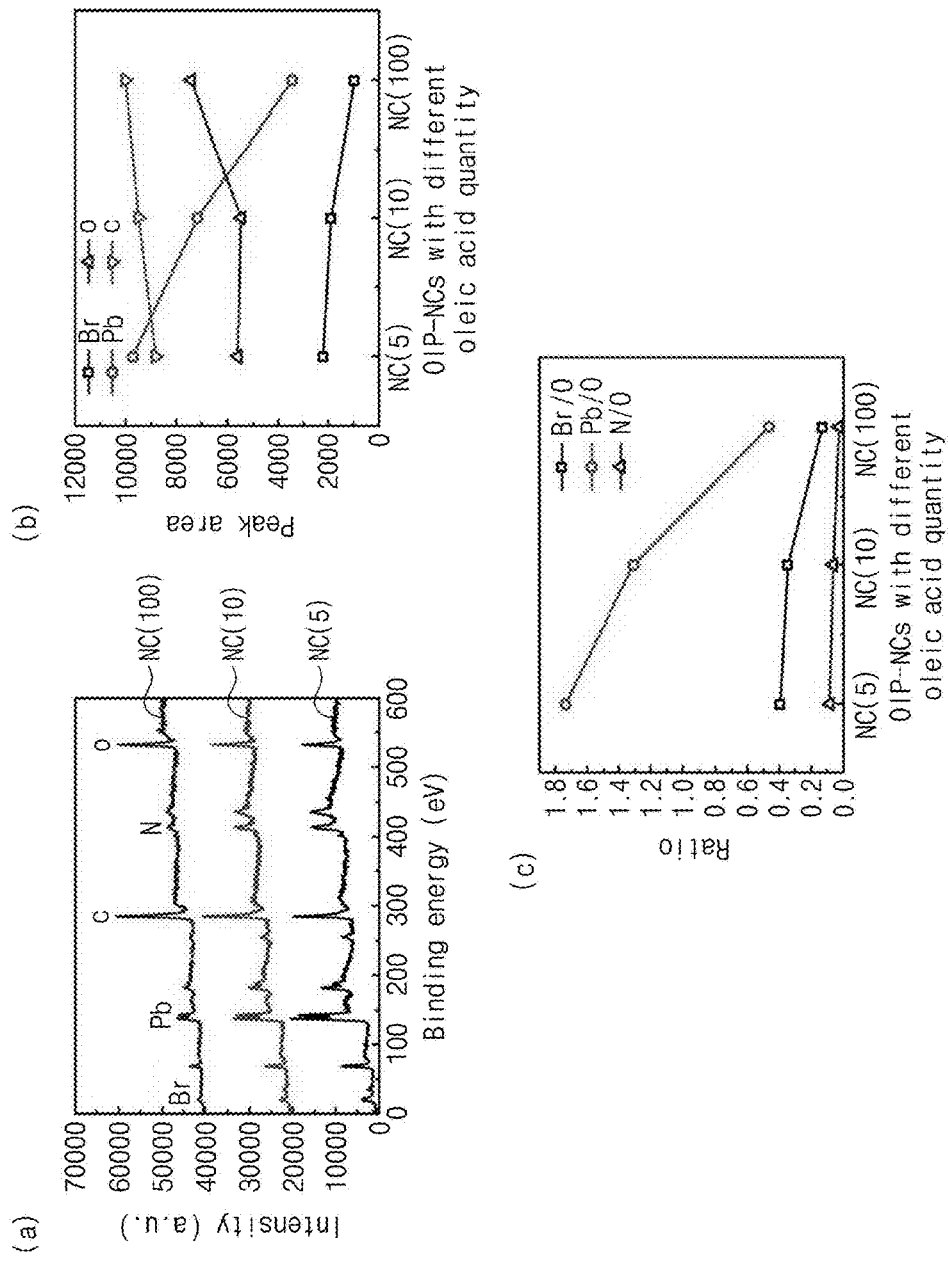
FIG. 21 is element analysis data depending on a size according to Manufacturing Example 30.

FIG. 21 is element analysis data depending on a size according to Manufacturing Example 1.

Referring to FIGS. 21(a) to 21(c), as the size of the nanocrystal decreases, a surface-to-volume ratio increases. Thus, an oleic acid that is a surfactant existing much at a small size may adhere, and thus, ratios of oxygen and carbon increases. On the other hand, it is seen that Br, Pb, and N, which relatively occupy the inside of the nanocrystal, decreases.

Figure 22:
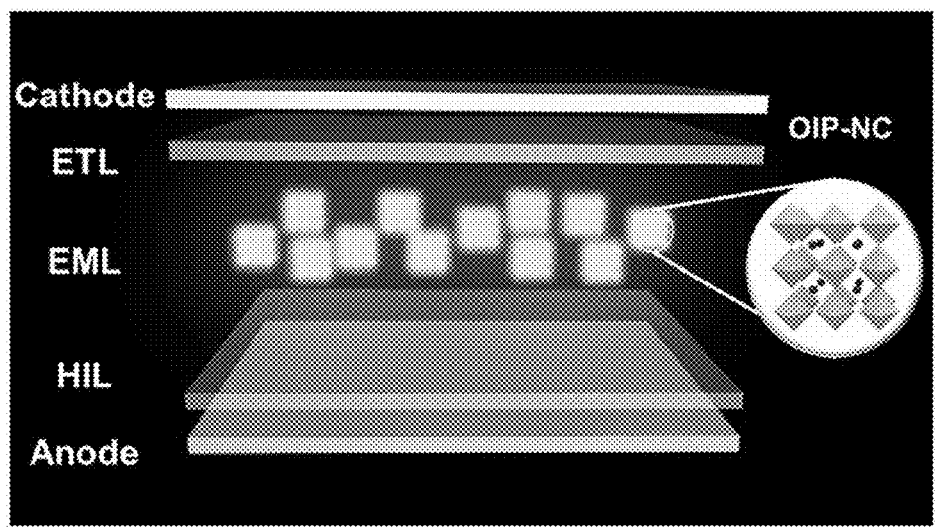
FIG. 22 is a schematic view illustrating a structure of a light emitting diode formed according to Manufacturing Example 30.

FIG. 22 is a schematic view illustrating a structure of a light emitting diode in which the nanocrystal is used as a light emitting layer.

Referring to FIG. 22, a light emitting diode includes an anode, a hole injection layer, a nanocrystal particle light emitting layer, an electron injection layer, and a cathode.

Figure 23:
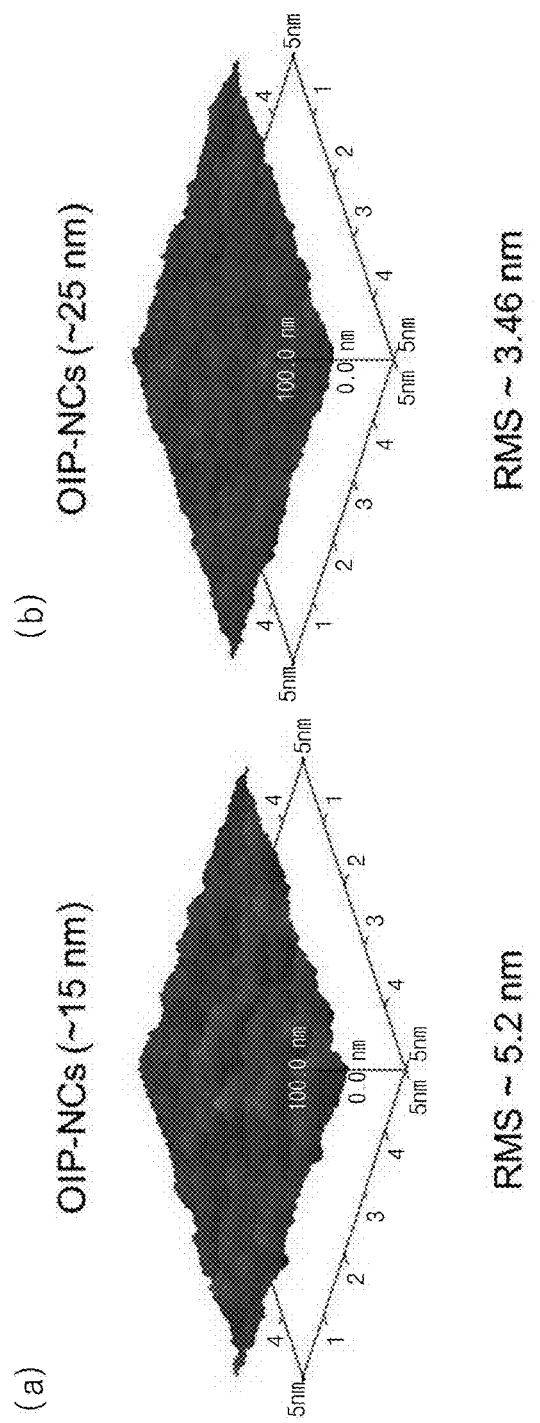
FIG. 23 is data obtained by forming the organic-inorganic-hybrid perovskite nanocrystal into a thin film according to Manufacturing Example 30.

FIG. 23 is data obtained by measuring roughness after the nanocrystal particle is formed in the form of a thin film. Referring to FIGS. 23(a) and 23(b), it is seen that roughness RMS of the thin film decreases to about 5.2 nm to about 3.46 nm when a thickness of a nanocrystal particle OIP-NCs increases to about 15 nm to about 25 nm.

Figure 24:
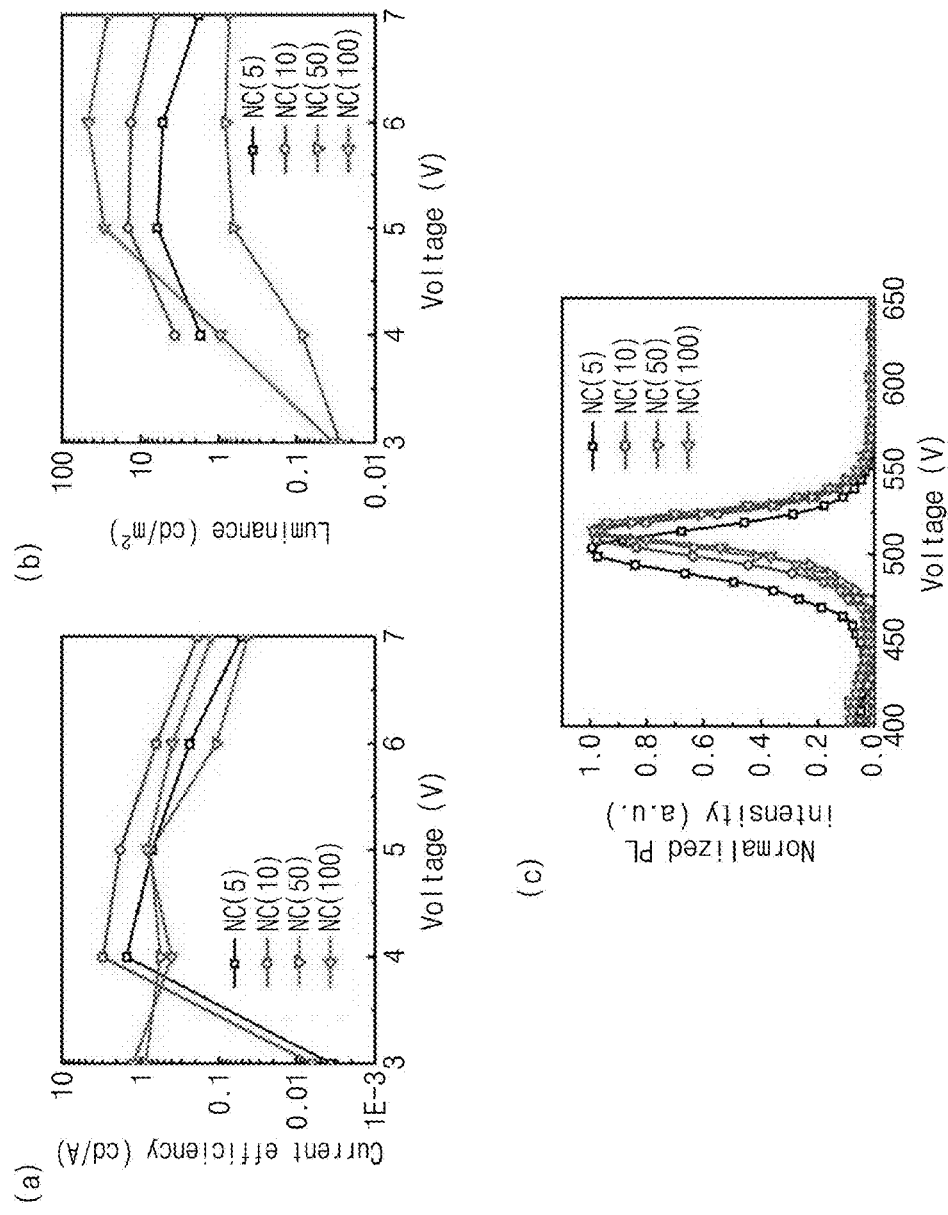
FIG. 24 is data illustrating performance of the light emitting diode having various sizes, which is formed according to Manufacturing Example 30.

FIG. 24 is data illustrating device performance of the light emitting diode implemented by using nanocrystal particle having various sizes.

Referring to FIGS. 24(a) to 24(c), it is seen that a light emitting diode using the nanocrystal (NC(10)) having a size near to or greater than the Bohr exciton diameter has maximum efficiency and maximum brightness. This is done because the photoluminescence quantum efficiency is maximized when the size is near to or greater than the Bohr exciton diameter. Particularly, although the photoluminescence spectrum moves to a short wavelength as the size of the nanocrystal particle as the size of the nanocrystal particle decreases, the photoluminescence spectrum of the device has a predetermined value. This is done because thermalization occurs with the lowest energy bandgap to emit light as electrons and holes move to the light emitting layer.

Figure 25:
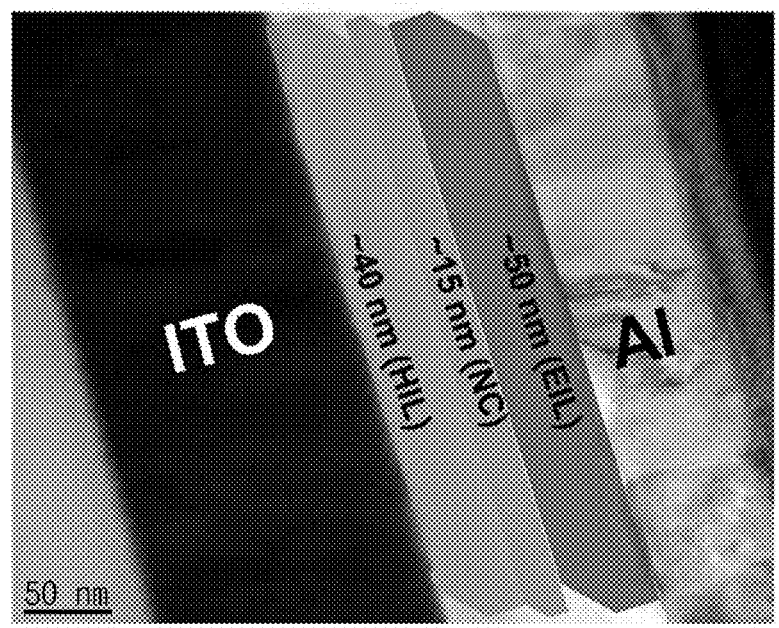
FIG. 25 is a side image of the light emitting diode formed according to Manufacturing Example 30.

FIG. 25 is an image displaying a cross section of the nanocrystal particle light emitting diode.

Referring to FIG. 25, it is seen that a hole injection layer HIL having a thickness of about 40 nm, a light emitting layer having a thickness of about 15 nm, and an electron injection layer EIL having a thickness of about 50 nm are formed between an anode ITO and a cathode Al.

Figure 26:
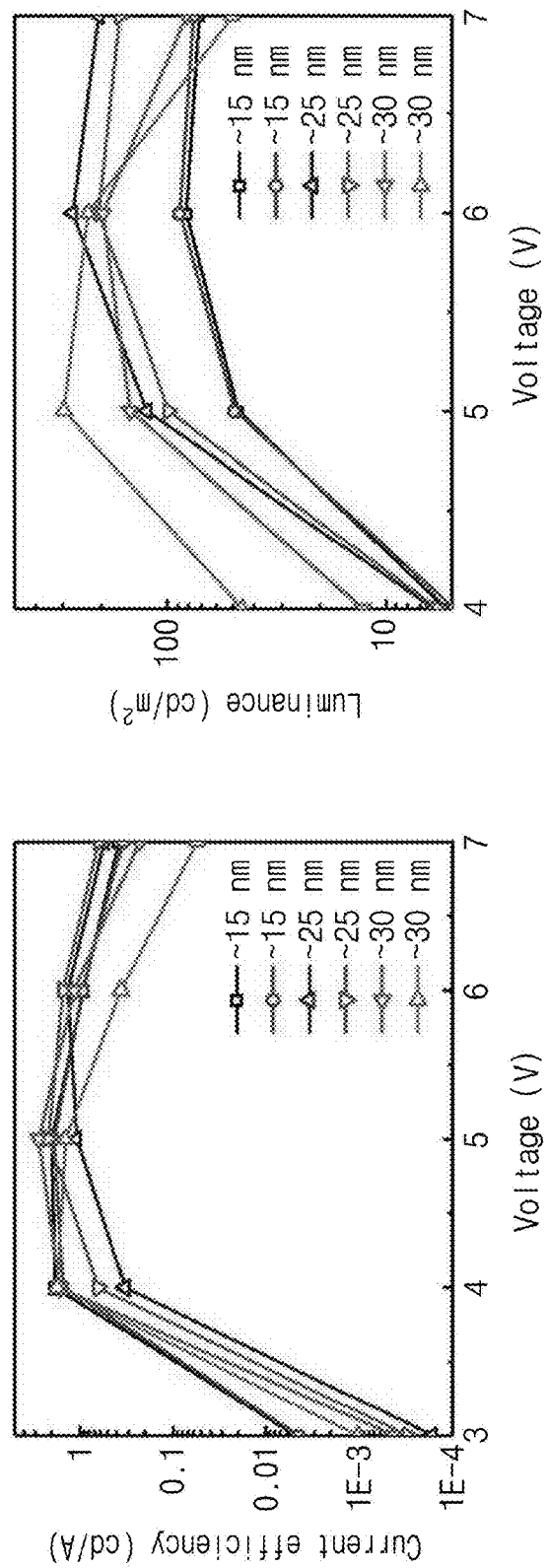
FIG. 26 is data illustrating performance of the light emitting diode depending on a variation in thickness of a thin film according to Manufacturing Example 30.

FIG. 26 is performance data of a light emitting diode depending on an increase in thickness of a nanocrystal particle.

Referring to FIG. 26, as a perovskite nanocrystal particle increases in thickness, surface roughness may be reduced, and also an amount of nanocrystal particle that is capable of emitting light increases to improve luminescence efficiency and brightness.

The perovskite nanocrystal structure having the crystal structure, in which the FCC and the BCC are combined with each other, may be formed in the organic-inorganic-hybrid perovskite or the inorganic metal halide perovskite nanocrystal particle, and the organic plane and the inorganic plane may be alternately stacked to form the lamellar structure. Particularly, since the organic ammonium without having the bandgap is used as the organic material, the excitons may be confined to the inorganic plane to implement the high color purity.

Also, the exciton diffusion length may be reduced, and the exciton binding energy may increase in the nanocrystal particle having a size of 10 nm to 30 nm to prevent the excitons from being annihilated by the thermal ionization and the delocalization of the charge carriers, thereby improving the luminescence efficiency at room temperature.

Also, the band gap energy of the organic-inorganic-hybrid perovskite nanocrystal particle or the inorganic metal halide perovskite nanocrystal particle may be determined by the crystalline structure without depending on the particle size.

Also, the organic-inorganic-hybrid perovskite nanocrystal particle or the inorganic metal halide perovskite nanocrystal particle may be nanoparticle that is capable of being dispersible in the organic solvent and thus applied to the various optoelectronic devices.

Also, the organic-inorganic-hybrid perovskite nanocrystal particle or the inorganic metal halide perovskite nanocrystal particle may be doped to increase the luminescence efficiency and the durability(stability) as well as convert the semiconductor type into the n-type or the p-type, and thereby to adjust the opto-electrical properties.

It should be noted that the embodiments of the present invention disclosed in the present specification and drawings are only illustrative of specific examples for the purpose of understanding and are not intended to limit the scope of the present invention. It is to be understood by those skilled in the art that other modifications based on the technical idea of the present invention are possible in addition to the embodiments disclosed herein.

DESCRIPTION OF SYMBOLS

100: Perovskite nanocrystal particle
100': Perovskite nanocrystal particle having core-shell structure
100'': Perovskite nanocrystal particle having structure with gradient composition 110: Perovskite nanocrystal structure
111: Doping element 115: Core
120: Organic ligand 130: Shell
140: Organic-inorganic-hybrid perovskite nanocrystal structure having gradient composition

The invention claimed is:

1. A perovskite nanocrystal particle capable of being dispersible in an organic solvent and comprising a perovskite nanocrystal structure,
wherein the perovskite nanocrystal particle is an organic-inorganic-hybrid perovskite or an inorganic metal halide perovskite, and
the perovskite nanocrystal particle has a diameter greater than a Bohr exciton diameter on an area that is not affected by a quantum confinement effect.

2. The perovskite nanocrystal particle of claim 1, wherein a light emitting body of the perovskite nanocrystal particle has a diameter of 20 nm to 30 nm.

3. The perovskite nanocrystal particle of claim 1, wherein the organic solvent comprises a polar solvent and a non-polar solvent,
the polar solvent comprises dimethylformamide, gamma butyrolactone, N-methylpyrrolidone, dimethylsulfoxide or isopropyl alcohol, and
the non-polar solvent comprises dichloroethylene, trichlorethylene, chloroform, chlorobenzene, dichlorobenzene, styrene, xylene, toluene, or cyclohexene.

4. The perovskite nanocrystal particle of claim 1, wherein the light-emitter has an emission wavelength of 200 nm to 1300 nm.

5. The perovskite nanocrystal particle of claim 1, wherein the perovskite nanocrystal particle has a spherical, cylindrical, cylindroid, polyprism or two-dimensional shape.

6. The perovskite nanocrystal particle of claim 1, wherein the perovskite nanocrystal particle has bandgap energy determined by the crystal structure without depending on the particle size.

7. The perovskite nanocrystal particle of claim 1, wherein the perovskite nanocrystal particle has bandgap energy of 1 eV to 5 eV.

8. The perovskite nanocrystal particle of claim 1, wherein the nanocrystal particle has a core-shell structure.

9. The perovskite nanocrystal particle of claim 1, wherein the nanocrystal particle has a structure with a gradient composition.

10. A light emitting device comprising:
a first electrode;
a second electrode; and
a light emitting layer disposed between the first electrode and the second electrode and comprising the perovskite nanocrystal particle of claim 1.

11. A solar cell comprising:
a first electrode;
a second electrode; and
a photoactive layer disposed between the first electrode and the second electrode and comprising the perovskite nanocrystal particle of claim 1.

12. The perovskite nanocrystal particle of claim 1, wherein the perovskite has a structure of $ABX_3$, $A_2BX_4$, $ABX_4$, or $A_{n-1}BnX_{3n+1}$ (where n is an integer between 2 to 6), and
the A is an organic ammonium or alkali material, the B is a metal material, the X is a halogen element.

13. The perovskite nanocrystal particle of claim 12, wherein the organic ammonium is amidinium group $((CH(NH_2)_2)$, $C_xH_{2x+1}(CNH_3)$, organic ions, $(CH_3NH_3)_n$, $((C_xH_{2x+1})_nNH_3)_n(CH_3NH_3)_n$, $R(NH_2)_2$ (R=alkyl), $(C_nH_{2n+1}NH_3)_n$, $CF_3NH_3$, $(CF_3NH_3)_n$, $((C_xF_{2x+1})_nNH_3)_n(CF_3NH_3)_n$, $((C_xF_{2x+1})_nNH_3)_n$, $(C_nF_{2n+1}NH_3)_n$) or a combination or a derivative thereof (where n is an integer equal to or greater than 1, and x is an integer equal to or greater than 1),
the alkali metal material is Na, K, Rb, Cs, or Fr or a combination thereof,
the B is a divalent transition metal, a rare earth metal, an alkali earth metal, Pb, Sn, Ge, Ga, In, Al, Sb, Bi, Po, or a combination thereof, and
the X is Cl, Br, I, or a combination thereof.

14. The perovskite nanocrystal particle of claim 1, further comprising a plurality of organic ligands surrounding a surface of the perovskite nanocrystal particle.

15. The perovskite nanocrystal particle of claim 14, wherein each of the organic ligands comprises alkyl halide or a carboxylic acid.

16. The perovskite nanocrystal particle of claim 14, wherein an alkyl structure of the alkyl halide comprises acyclic alkyl having a structure of $C_nH_{2n+1}$, primary alcohol, secondary alcohol, tertiary alcohol, alkylamine, p-substituted aniline, phenyl ammonium, or fluorine ammonium, and
the carboxylic acid comprises a 4,4'-Azobis(4-cyanovaleric acid), an acetic acid, a 5-aminosalicylic acid, an acrylic acid, an L-aspentic acid, a 6-bromohexanoic acid, a bromoacetic acid, a dichloro acetic acid, an ethylenediaminetetraacetic acid, an isobutyric acid, an itaconic acid, a maleic acid, an r-maleimidobutyric acid, an L-malic acid, a 4-Nitrobenzoic acid, a 1-pyrenecarboxylic acid, or an oleic acid.

17. The perovskite nanocrystal particle of claim 1, wherein the perovskite is a doped perovskite.

18. The perovskite nanocrystal particle of claim 17, wherein the doped perovskite comprises a structure of $ABX_3$, $A_2BX_4$, $ABX_4$, or $A_{n-1}BnX_{3n+1}$ (where n is an integer between 2 to 6), where a portion of the A is substituted with A', a portion of the B is substituted with B', or a portion of the X is substituted with X', and
the A and A' are organic ammonium, and the B and B' are metal materials, and X and X' are halogen elements.

19. The perovskite nanocrystal particle of claim 18, wherein the A and A' are $(CH_3NH_3)_n$, $((C_xH_{2x+1})_nNH_3)_n(CH_3NH_3)_n$, $R(NH_2)_2$ (R=alkyl), $(C_nH_{2n+1}NH_3)_n$, $CF_3NH_3$, $(CF_3NH_3)_n$, $((C_xF_{2x+1})_nNH_3)_n(CF_3NH_3)_n$, $((C_xF_{2x+1})_nNH_3)_n$, $(C_nF_{2n+1}NH_3)_n$ or a derivative thereof (where n is an integer equal to or greater than 1, and x is an integer equal to or greater than 1),
each of the B and B' is a divalent transition metal, a rare earth metal, an alkali earth metal, Pb, Sn, Ge, Ga, In, Al, Sb, Bi, or Po, and
the X and X' are Cl, Br, or I.

20. The perovskite nanocrystal particle of claim 18, wherein a ratio at which a portion of the A is substituted with A', a portion of the B is substituted with B', or a portion of the X is substituted with X' is 0.1% to 5%.

* * * * *